(12) United States Patent
Djupesland et al.

(10) Patent No.: US 10,525,218 B2
(45) Date of Patent: Jan. 7, 2020

(54) NASAL DELIVERY DEVICES

(71) Applicant: OptiNose AS, Oslo (NO)

(72) Inventors: Per Gisle Djupesland, Oslo (NO); Colin David Sheldrake, Wiltshire (GB); Simon Smith, Cambridge (GB); Rachel Striebig, Cambridge (GB); Andy Pidgeon, Cambridge (GB); Tom St. Quintin, Cambridge (GB)

(73) Assignee: OptiNose AS, Oslo (NO)

( * ) Notice: Subject to any disclaimer, the term of this patent is extended or adjusted under 35 U.S.C. 154(b) by 1116 days.

(21) Appl. No.: 14/674,103

(22) Filed: Mar. 31, 2015

(65) Prior Publication Data
US 2016/0051778 A1 Feb. 25, 2016

Related U.S. Application Data

(63) Continuation of application No. 12/516,404, filed as application No. PCT/GB2007/004571 on Nov. 28, 2007, now Pat. No. 9,010,325.

(30) Foreign Application Priority Data

Nov. 28, 2006 (GB) .................................. 0623732.5

(51) Int. Cl.
*A61M 15/08* (2006.01)
*A61M 15/00* (2006.01)
*A61M 16/10* (2006.01)

(52) U.S. Cl.
CPC ........ *A61M 15/08* (2013.01); *A61M 15/0018* (2014.02); *A61M 15/0021* (2014.02);
(Continued)

(58) Field of Classification Search
CPC .............. A61M 15/08; A61M 15/0043; A61M 15/003; A61M 15/0026; A61M 15/0096;
(Continued)

(56) References Cited

U.S. PATENT DOCUMENTS 605,436 A 6/1898 Kellogg
642,748 A 2/1900 Manners
(Continued)

FOREIGN PATENT DOCUMENTS

EP 1 410 820 A2 4/2004
GB 2 395 909 A 6/2004
(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Colin W Stuart
*Assistant Examiner* — Douglas Y Sul
(74) *Attorney, Agent, or Firm* — Finnegan, Henderson, Farabow, Garrett & Dunner, LLP

(57) ABSTRACT

A nasal delivery device for and method of delivering particulate substance to the nasal airway of a subject. The delivery device includes a body assembly including a mouthpiece unit which includes a mouthpiece through which the subject in use exhales, and a substance-supply unit which is fluidly connected to the mouthpiece unit and actuatable to provide particulate substance for delivery to the nasal airway of the subject. The body assembly is configured to receive a replaceable nosepiece unit which includes a nosepiece and contains a container containing particulate substance.

9 Claims, 24 Drawing Sheets

(52) U.S. Cl.
CPC .... *A61M 15/0026* (2014.02); *A61M 15/0028* (2013.01); *A61M 15/0035* (2014.02); *A61M 15/0041* (2014.02); *A61M 15/0043* (2014.02); *A61M 15/0081* (2014.02); *A61M 15/0098* (2014.02); *A61M 16/1045* (2013.01); *A61M 2202/064* (2013.01); *A61M 2205/0222* (2013.01); *A61M 2210/0618* (2013.01); *A61M 2210/0625* (2013.01)

(58) Field of Classification Search
CPC ........ A61M 15/0098; A61M 2202/064; A61M 2210/0618
See application file for complete search history.

(56) References Cited

U.S. PATENT DOCUMENTS

| | | | |
|---|---|---|---|
| 658,436 | A | 9/1900 | Groth |
| 746,749 | A | 12/1903 | Seidel |
| 794,641 | A | 7/1905 | Ramey |
| 902,832 | A | 11/1908 | Philbrook |
| 3,949,751 | A | 4/1976 | Birch et al. |
| 4,013,075 | A | 3/1977 | Cocozza |
| 4,206,758 | A * | 6/1980 | Hallworth ......... A61M 15/0028 128/203.15 |
| 4,210,140 | A * | 7/1980 | James ............... A61M 15/0028 604/58 |
| 4,338,931 | A | 7/1982 | Cavazza |
| 4,889,114 | A | 12/1989 | Kladders |
| 5,498,255 | A * | 3/1996 | Wong ................ A61K 9/0004 424/453 |
| 5,562,918 | A * | 10/1996 | Stimpson .......... A61M 15/0028 128/200.24 |
| 5,685,294 | A | 11/1997 | Gupte et al. |
| 5,797,392 | A | 8/1998 | Keldmann et al. |
| 5,921,236 | A | 7/1999 | Ohki et al. |
| 6,648,848 | B1 | 11/2003 | Keldmann et al. |
| 6,715,485 | B1 | 4/2004 | Djupesland |
| 6,877,672 | B2 | 4/2005 | Stihl |
| D530,815 | S | 10/2006 | Murphy et al. |
| 7,284,553 | B2 | 10/2007 | Hochrainer |
| 7,306,116 | B2 | 12/2007 | Fuchs |
| 7,347,201 | B2 | 3/2008 | Djupesland |
| 7,377,901 | B2 | 5/2008 | Djupesland et al. |
| 7,464,706 | B2 * | 12/2008 | Steiner .............. A61M 15/0028 128/203.12 |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland et al. |
| 7,975,690 | B2 | 7/2011 | Djupesland |
| 8,047,202 | B2 | 11/2011 | Djupesland |
| 8,146,589 | B2 | 4/2012 | Djupesland |
| 8,171,929 | B2 | 5/2012 | Djupesland et al. |
| 8,327,844 | B2 | 12/2012 | Djupesland |
| 8,511,303 | B2 | 8/2013 | Djupesland |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,590,530 | B2 | 11/2013 | Djupesland et al. |
| 8,596,278 | B2 | 12/2013 | Djupesland |
| 8,800,555 | B2 | 8/2014 | Djupesland |
| 8,875,704 | B2 | 11/2014 | Djupesland et al. |
| 8,899,229 | B2 | 12/2014 | Djupesland et al. |
| 8,910,629 | B2 | 12/2014 | Djupesland et al. |
| D723,156 | S | 2/2015 | Djupesland et al. |
| D725,769 | S | 3/2015 | Djupesland et al. |
| 8,978,647 | B2 | 3/2015 | Djupesland et al. |
| 9,010,325 | B2 | 4/2015 | Djupesland et al. |
| 9,038,630 | B2 | 5/2015 | Djupesland et al. |
| 9,067,034 | B2 | 6/2015 | Djupesland et al. |
| 9,072,857 | B2 | 7/2015 | Djupesland |
| 9,108,015 | B2 | 8/2015 | Djupesland |
| 9,119,932 | B2 | 9/2015 | Djupesland |
| 9,132,249 | B2 | 9/2015 | Djupesland |
| 9,144,652 | B2 | 9/2015 | Djupesland et al. |
| 9,168,341 | B2 | 10/2015 | Djupesland |
| 9,205,208 | B2 | 12/2015 | Djupesland |
| 9,205,209 | B2 | 12/2015 | Djupesland |
| 9,272,104 | B2 | 3/2016 | Djupesland |
| D759,805 | S | 6/2016 | Djupesland |
| D761,951 | S | 7/2016 | Djupesland |
| 9,452,272 | B2 | 9/2016 | Djupesland et al. |
| 9,468,727 | B2 | 10/2016 | Djupesland |
| D773,644 | S | 12/2016 | Djupesland |
| 9,522,243 | B2 | 12/2016 | Djupesland |
| 9,566,402 | B2 | 2/2017 | Djupesland |
| 9,649,456 | B2 | 5/2017 | Djupesland et al. |
| D809,128 | S | 1/2018 | Djupesland |
| 2001/0020472 | A1 * | 9/2001 | Horlin ............... A61M 15/0028 128/203.15 |
| 2004/0024330 | A1 | 2/2004 | Djupesland et al. |
| 2004/0112378 | A1 | 6/2004 | Djupesland |
| 2004/0112379 | A1 | 6/2004 | Djupesland |
| 2004/0112380 | A1 | 6/2004 | Djupesland |
| 2004/0149289 | A1 | 8/2004 | Djupesland |
| 2004/0182388 | A1 | 9/2004 | Djupesland |
| 2005/0028812 | A1 | 2/2005 | Djupesland |
| 2005/0072430 | A1 * | 4/2005 | Djupesland ....... A61M 15/0091 128/206.11 |
| 2005/0235992 | A1 | 10/2005 | Djupesland |
| 2006/0096589 | A1 | 5/2006 | Djupesland |
| 2006/0107957 | A1 | 5/2006 | Djupesland |
| 2006/0169278 | A1 | 8/2006 | Djupesland et al. |
| 2006/0219240 | A1 | 10/2006 | Djupesland |
| 2006/0219241 | A1 | 10/2006 | Djupesland |
| 2006/0225732 | A1 | 10/2006 | Djupesland |
| 2006/0231094 | A1 | 10/2006 | Djupesland |
| 2007/0039614 | A1 | 2/2007 | Djupesland |
| 2007/0125371 | A1 | 6/2007 | Djupesland |
| 2007/0186927 | A1 | 8/2007 | Djupesland et al. |
| 2008/0161771 | A1 | 7/2008 | Djupesland |
| 2008/0163874 | A1 | 7/2008 | Djupesland |
| 2008/0221471 | A1 | 9/2008 | Djupesland et al. |
| 2008/0223363 | A1 | 9/2008 | Djupesland |
| 2008/0289629 | A1 | 11/2008 | Djupesland et al. |
| 2009/0101146 | A1 | 4/2009 | Djupesland |
| 2009/0293873 | A1 | 12/2009 | Djupesland et al. |
| 2009/0304802 | A1 | 12/2009 | Djupesland et al. |
| 2009/0314293 | A1 | 12/2009 | Djupesland |
| 2009/0320832 | A1 | 12/2009 | Djupesland |
| 2010/0035805 | A1 | 2/2010 | Hafner |
| 2010/0051022 | A1 | 3/2010 | Djupesland |
| 2010/0057047 | A1 | 3/2010 | Djupesland et al. |
| 2010/0199984 | A1 | 8/2010 | Williams et al. |
| 2010/0242959 | A1 | 9/2010 | Djupesland et al. |
| 2010/0282246 | A1 | 11/2010 | Djupesland et al. |
| 2010/0288275 | A1 | 11/2010 | Djupesland et al. |
| 2010/0300439 | A1 | 12/2010 | Djupesland et al. |
| 2011/0023869 | A1 | 2/2011 | Djupesland |
| 2011/0053827 | A1 | 3/2011 | Hafner |
| 2011/0088690 | A1 | 4/2011 | Djupesland et al. |
| 2011/0088691 | A1 | 4/2011 | Djupesland |
| 2011/0114087 | A1 | 5/2011 | Djupesland et al. |
| 2011/0120456 | A1 | 5/2011 | Immel |
| 2011/0126830 | A1 | 6/2011 | Djupesland et al. |
| 2011/0259329 | A1 | 10/2011 | Djupesland et al. |
| 2011/0318345 | A1 | 12/2011 | Djupesland |
| 2012/0000459 | A1 | 1/2012 | Djupesland |
| 2012/0006323 | A1 | 1/2012 | Djupesland |
| 2012/0073571 | A1 | 3/2012 | Djupesland |
| 2012/0090608 | A1 | 4/2012 | Djupesland et al. |
| 2012/0260915 | A1 | 10/2012 | Djupesland |
| 2013/0098362 | A1 | 4/2013 | Djupesland et al. |
| 2013/0125889 | A1 | 5/2013 | Djupesland et al. |
| 2013/0327320 | A1 | 12/2013 | Djupesland |
| 2014/0018295 | A1 | 1/2014 | Djupesland |
| 2014/0041660 | A1 | 2/2014 | Djupesland et al. |
| 2014/0060536 | A1 | 3/2014 | Djupesland |

(56) References Cited

U.S. PATENT DOCUMENTS

| | | |
|---|---|---|
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095989 A1 | 4/2016 | Djupesland |
| 2016/0095993 A1 | 4/2016 | Djupesland |
| 2016/0101249 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |
| 2017/0274164 A1 | 9/2017 | Djupesland et al. |
| 2017/0333649 A1 | 11/2017 | Djupesland |

FOREIGN PATENT DOCUMENTS

| | | |
|---|---|---|
| GB | 2 397 025 A | 7/2004 |
| GB | 2 418 147 A | 3/2006 |
| GB | 2 424 587 A | 10/2006 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

G. Furness, *Nasal Drug Delivery: Rapid Onset via a Convenient Route*, ONdrugDelivery Ltd. (2005).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

(56) References Cited

OTHER PUBLICATIONS

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

\* cited by examiner

NASAL DELIVERY DEVICES

This is a continuation application of U.S. application Ser. No. 12/516,404, filed Jun. 21, 2010, which is the national stage entry of PCT/GB2007/04571, filed Nov. 28, 2007, which claims priority to GB 0623732.5 filed on Nov. 28, 2006, the entire contents of each of which are incorporated herein by reference.

The present invention relates to a nasal delivery device for and method of delivering particulate substance, in particular a powdered substance, to the nasal airway of a subject, and a container for use with the same.

There is an increasing interest in the nasal delivery of substances, typically pharmaceutical drugs, both as powders and liquids, for topical and systemic delivery.

Current delivery systems are not suited to the delivery of substances to the upper posterior region of the nasal airway, in particular targeted delivery to the olfactory region and the sinus ostia.

U.S. Pat. Nos. 4,013,075 and 4,889,114 disclose examples of prior art inhalation devices, which provide for the inhalation of a powdered substance from a capsule.

WO-A-00/051672, the content of which is herein incorporated by reference, discloses a delivery device for delivering a substance, in particular a medicament, in a bi-directional flow through the nasal cavities, that is, an air flow which passes into one nostril, around the posterior margin of the nasal septum and in the opposite direction out of the other nostril. A particular feature of this bi-directional mode of delivery is the ability to target defined regions in the nasal airway, for both topical and systemic delivery, in particular the upper posterior region which cannot be targeted with existing systems.

The present inventors have recognized that the delivery of powdered substances using the exhalation breath of a subject still presents a significant challenge.

It is an aim of the present invention to provide a delivery device which allows for delivery of powdered substances from containers, typically capsules or blisters, which contain a pre-metered dose of substance with the appropriate particle size distribution and surface properties, where using the exhalation breath of the subject.

In one aspect the present invention provides a nasal delivery device for delivering particulate substance to the nasal airway of a subject, the delivery device comprising: a body assembly including a mouthpiece unit which includes a mouthpiece through which the subject in use exhales, and a substance-supply unit which is fluidly connected to the mouthpiece unit and configured to receive a replaceable nosepiece unit which includes a nosepiece and contains a container containing particulate substance, wherein the substance-supply unit is actuatable to provide particulate substance for delivery to the nasal airway of the subject.

In one embodiment the delivery device further comprises: a replaceable nosepiece unit which includes a nosepiece for fitting to a nostril of a subject, and a container chamber which contains a container containing particulate substance.

In one embodiment the delivery device is configured to prevent operation until a nosepiece unit is fitted to the body assembly.

In one embodiment the body assembly includes an actuation mechanism which is manually actuatable by the subject to open the container, and the delivery device is configured to prevent actuation of the actuation mechanism until the nosepiece unit is fitted to the body assembly.

In one embodiment the substance-supply unit includes an interlock mechanism which adopts a first, locking configuration when a nosepiece unit is not fitted to the body assembly, in which the actuation mechanism is not actuatable, and a second, released configuration when a nosepiece unit is fitted to the body assembly, in which the actuation mechanism is actuatable.

In one embodiment the interlock mechanism comprises an interlock member which is movably disposed between locking and released positions and normally biased to the locking position.

In one embodiment the substance-supply unit includes a valve unit which is operable between a first, closed configuration in which a fluid communication path with the mouthpiece is closed, and a second, open configuration in which the fluid communication path is open.

In one embodiment the interlock mechanism is configured to lock the valve unit in the closed configuration when the interlock mechanism is in the locking configuration and allow operation of the valve unit when the interlock mechanism is in the released configuration.

In one embodiment the valve unit includes a locking element which is engaged by the interlock mechanism when the interlock mechanism is in the locking configuration to prevent operation of the valve unit.

In another aspect the present invention provides a nasal delivery device for delivering particulate substance to the nasal airway of a subject, the delivery device comprising: a mouthpiece unit which includes a mouthpiece through which the subject in use exhales; a nosepiece unit which includes a nosepiece for fitting to a nostril of the subject; and a substance-supply unit which is configured to receive a container containing particulate substance and operable to provide a metered amount of substance in fluid communication with the mouthpiece and nosepiece units, such that an exhalation air flow delivered through the substance-supply unit entrains the substance.

In one embodiment the container comprises first and second parts which together define an enclosed chamber and are movable between a first, closed configuration in which the container is closed and a second, open configuration in which the container is open, and the substance-supply unit is operable to move the first and second parts of the container to the open configuration.

In one embodiment the first and second parts of the container are slideably disposed relative to one another and each include at least one aperture, which are closed with the first and second parts in the closed configuration and opened by sliding of the first and second parts to the open configuration.

In one embodiment the substance-supply unit comprises a support member, and a body section which is movable relative to the support member between a first, container-receiving position for receiving a container in the closed configuration, and a second, operative position in which the container is opened and disposed in fluid communication with the mouthpiece and nosepiece units.

In one embodiment the body section is rotatably disposed to the support member.

In one embodiment the body section includes a container-receiving aperture, which allows for introduction of a container thereinto when the body section is in the container-receiving position and is closed when the body section is in the operative position.

In one embodiment one of the support member and the body section includes an inlet aperture which is fluidly isolated from the mouthpiece unit when the body section is in the container-receiving position and fluidly connected to the mouthpiece unit when the body section is in the operative position.

In one embodiment the support member and the body section each include an engagement feature for engaging respective ones of the first and second parts of the container, and the support member and the body section are axially movable relative to one another, such that, on movement of the body section from the container-receiving position to the operative position, the first and second parts of the container are moved to the open configuration.

In one embodiment the support member and the body section are coupled by a cam mechanism, which provides that the engagement features thereof are moved between a first spacing in which the container is received therebetween, a second, closer spacing in which the first and second parts of the container are moved to the open configuration, and a third spacing in which the container is moveable axially between the engagement features.

In one embodiment the delivery device further comprises: a housing which supports the mouthpiece unit, the nosepiece unit and the substance-supply unit.

In one embodiment the substance-supply unit includes a container-receiving member which is movably disposed to the housing between an open position for enabling loading of a container thereinto, and a closed position in which the container is contained within the housing.

In one embodiment the container-receiving member includes a cavity which defines an air flow channel between the mouthpiece and nosepiece units, such that an air flow is delivered therethrough on exhalation by the subject through the mouthpiece, and a support section for supporting the container in the cavity.

In one embodiment the container comprises a main body part and first and second bearing support parts at the respective ends of the body part, and the support section includes first and second container supports for rotatably supporting the respective support parts of the container.

In one embodiment the support parts of the container comprise part-spherical projections and the container supports comprise part-spherical recesses.

In one embodiment the substance-supply unit includes a locking mechanism for locking the container-receiving member in the closed position.

In a further aspect the present invention provides a nasal delivery device for delivering particulate substance to the nasal airway of a subject, the delivery device comprising: a body assembly including a mouthpiece unit which includes a mouthpiece through which the subject in use exhales, and a substance-supply unit which is fluidly connected to the mouthpiece unit and actuatable to provide particulate substance for delivery to the nasal airway of the subject; wherein the body assembly is configured to receive a replaceable nosepiece unit which includes a nosepiece and contains a container containing particulate substance.

In one embodiment the delivery device further comprises: a replaceable nosepiece unit which includes a nosepiece for fitting to a nostril of a subject, and a container chamber which contains a container containing particulate substance.

In one embodiment the delivery device is configured to prevent operation until a nosepiece unit is fitted to the body assembly.

In one embodiment the body assembly includes an actuation mechanism which is manually actuatable by the subject to open the container, and the delivery device is configured to prevent actuation of the actuation mechanism until the nosepiece unit is fitted to the body assembly.

In one embodiment the actuation mechanism is locked in a locked configuration when a nosepiece unit is not fitted to the body assembly, such as to prevent operation of the actuation mechanism.

In one embodiment the nosepiece unit includes a release member for releasing the actuation mechanism from the locked configuration on fitting the nosepiece unit to the body assembly.

In one embodiment the actuation mechanism includes an actuation member which is latched in a locked position in the locked configuration of the actuation mechanism, and the release member of the nosepiece unit is operative to release the latched actuation member on fitting the nosepiece unit to the body assembly.

In one embodiment the nosepiece unit is fitted to the body assembly in one, fitting sense and removed from the body assembly in the opposite, removal sense, and the release member includes a support element, an engagement element for engaging the actuation mechanism and a frangible connection element which connects the support element to the engagement element, wherein the engagement element presents a substantially rigid structure when the nosepiece unit is fitted in a first instance to the body assembly and is operative to release the actuation mechanism from the locked configuration, and is deformed on removing the nosepiece unit from the body assembly.

In one embodiment the body assembly further comprises a locking mechanism for locking the actuation mechanism from further operation following a predeterminable number of operations of the actuation mechanism.

In one embodiment the locking mechanism comprises a rotatable element which is indexed with each actuation of the actuation mechanism and locks the actuation mechanism to prevent further operation thereof following a predeterminable number of operations of the actuation mechanism.

In a yet further aspect the present invention provides a container comprising first and second body parts which together define an enclosed chamber and are movable between a first, closed configuration in which the container is closed and a second, open configuration in which the container is open.

In one embodiment the first and second body parts are slideably disposed relative to one another and each include at least one aperture, which are closed with the first and second body parts in the closed configuration and opened by sliding of the first and second body parts to the open configuration.

In one embodiment the first and second body parts include inter-engaging guides which provide for axial sliding of the first and second body parts without substantially any rotation thereof.

In one embodiment the container is an elongate container.

In one embodiment the container is a capsule.

In one embodiment the container is for containing particulate substance.

In a still further aspect the present invention provides a container comprising a main body part and first and second bearing support parts at the respective ends of the main body part which provide bearing supports about which the container is rotatable.

In one embodiment the support parts comprise part-spherical projections, and preferably substantially hemispherical projections.

In one embodiment the container is an elongate container.

In one embodiment the container is a capsule.

In one embodiment the container is for containing particulate substance.

Preferred embodiments of the present invention will now be described hereinbelow by way of example only with reference to the accompanying drawings, in which:

FIGS. 1 to 6 illustrate a delivery device in accordance with a first embodiment of the present invention.

Figure 1:
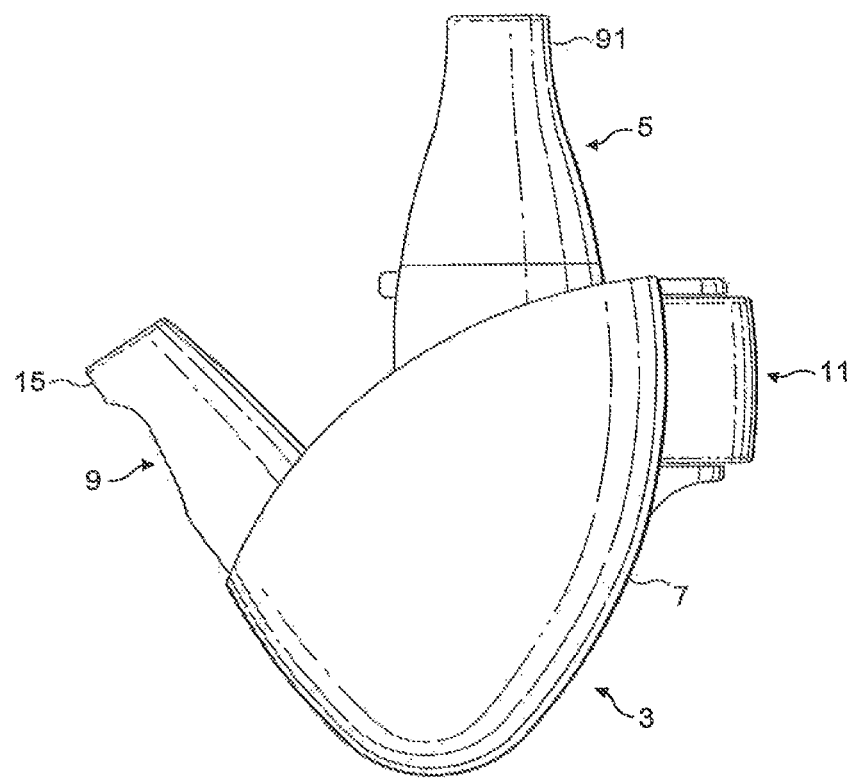
FIG. 1 illustrates a side view of a delivery device in accordance with a first embodiment of the present invention.
Figure 2:
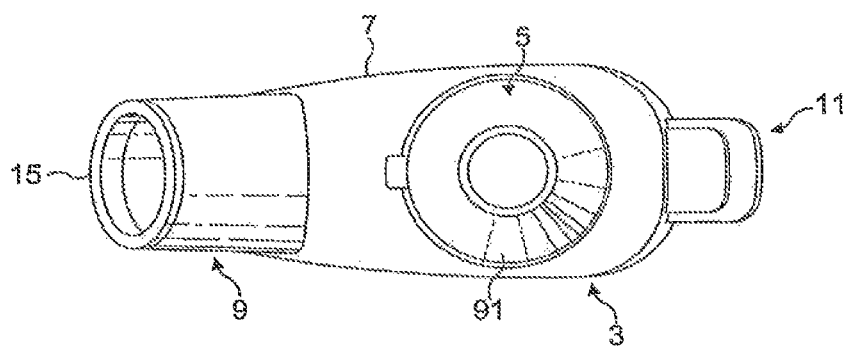
FIG. 2 illustrates a plan view of the delivery device of FIG. 1.

The delivery device comprises a main, body assembly 3 and a nosepiece unit 5, which contains a container C containing substance to be delivered to the nasal cavity of a subject and is removably fitted to the body assembly 3, such as to allow for re-use of the body assembly 3, as will be described in more detail hereinbelow.

In this embodiment the container C comprises a capsule, but could have any form which contains a metered dose of substance, such as a blister.

The body assembly 3 comprises a housing 7, a mouthpiece unit 9 and a substance-supply unit 11 which is fluidly connected to the mouthpiece unit 9 and to which the nosepiece unit 5 is fitted.

The mouthpiece unit 9 comprises a mouthpiece 15 which in use is gripped in the lips of a subject, and an air flow channel 17 which is fluidly connected to the substance-supply unit 11.

In this embodiment the housing 7 and the mouthpiece unit 9 are integrally formed, typically from a plastics material.

The substance-supply unit 11 comprises a body section 21 which receives the nosepiece unit 5, a rupturing mechanism 23 which is operable to rupture the container C as contained by the nosepiece unit 5, and an interlock member 25 which is operative to prevent operation of the rupturing mechanism 23 without the nosepiece unit 5 being fitted, or at least being fitted properly, to the body section 21.

The body section 21 comprises a body member 29 which includes a cavity 31, in this embodiment cylindrical in shape, an inlet 33 which is in fluid communication with the cavity 31 and fluidly connected to the air flow channel 17 of the mouthpiece unit 9, and an outlet 35 which is in fluid communication with the cavity 31 and fluidly connected to the nosepiece unit 5 when fitted to the body section 21. With this configuration, an exhalation air flow, as delivered through the mouthpiece unit 9, is delivered through the cavity 31 of the body section 21 and from the nosepiece unit 5.

The body section 21 further comprises a first guide 41, in this embodiment comprising a pair of laterally-extending slots 43 on opposed sides of the body member 29, which act to guide the rupturing mechanism 23 laterally to the body member 29 in rupturing the contained container C.

The body section 21 further comprises a second guide 45, in this embodiment comprising a first pair of longitudinally-extending slots 47 on opposed sides of the body member 29, which act to guide the interlock member 25 longitudinally to the body member 29, and a third longitudinally-extending slot 49, which slideably contains a contact element 87 of the interlock member 25 and receives a contact element 97 on the nosepiece unit 5 in providing for release of the interlock member 25, as will be described in more detail hereinbelow.

Figure 4:
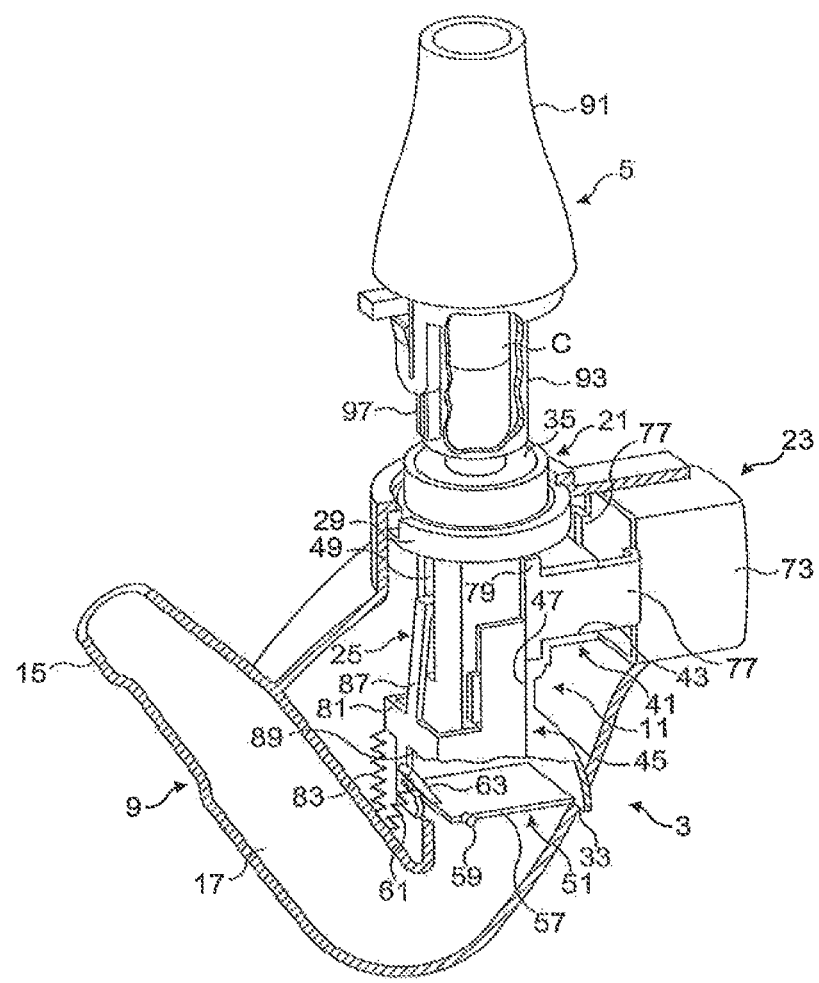
FIG. 4 illustrates the perspective view of FIG. 3, where part cut-away.
Figure 5:
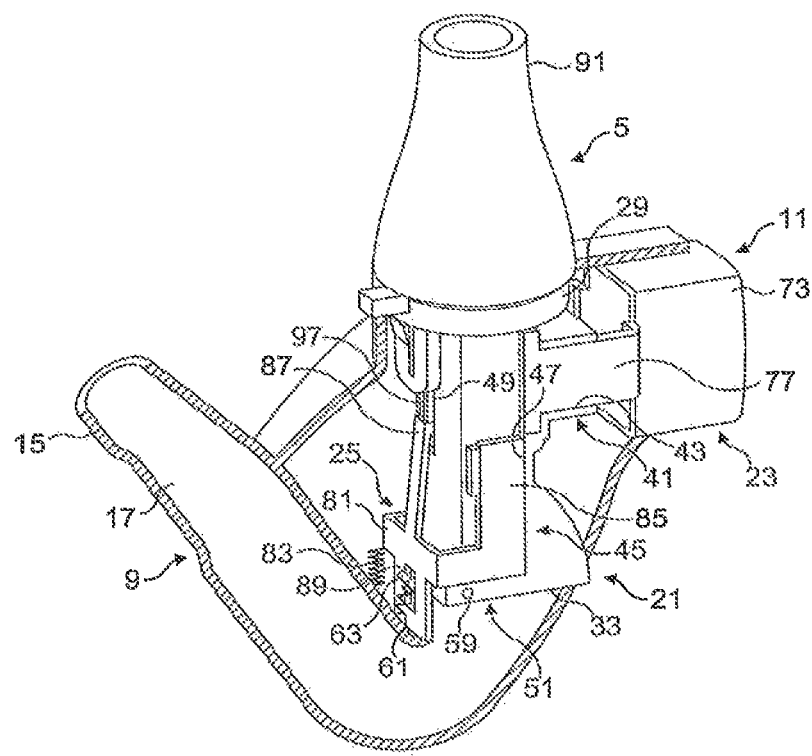
FIG. 5 illustrates a perspective view of the delivery device of FIG. 1, with the nosepiece unit fitted to the body assembly.
Figure 6:
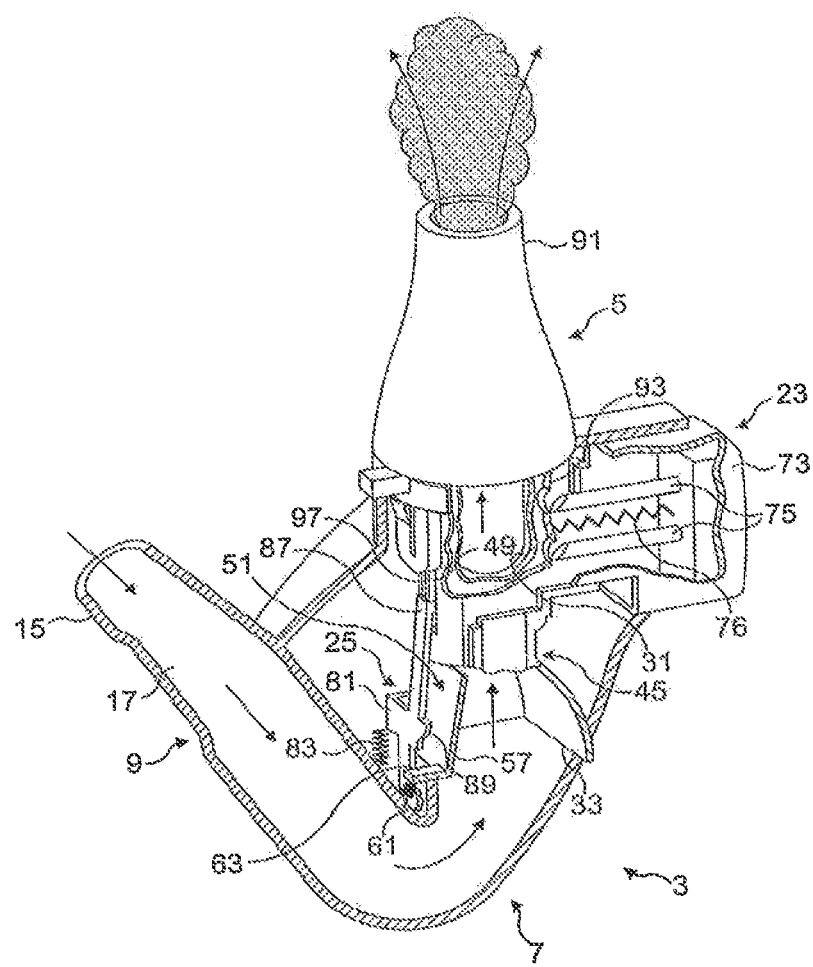
FIG. 6 illustrates a part cut-away fragmentary perspective view of the delivery device of FIG. 1 following exhalation by the subject through the mouthpiece.

The substance-supply unit 11 further comprises a valve 51 which is disposed at the inlet 33 of the body member 29 and operable between a first, closed position, as illustrated in FIG. 4, which substantially prevents an air flow through the cavity 31 of the body member 29, and a second, open position, as illustrated in FIG. 6, which allows for a flow through the cavity 31 of the body member 29.

In this embodiment the valve 51 is a pressure-sensitive valve which is such as to prevent an air flow through the cavity 31 until a predetermined pressure has been developed upstream thereof.

In this embodiment the valve 51 comprises a flap member 57 which is hingable about a pivot 59 and normally biased to a closed, sealing position by a resilient element 61, here a spring, such that a predetermined pressure is required to overcome the biasing force of the resilient element 61.

In this embodiment the flap member 57 includes a locking element 63, here in the form of an arm, which is operably coupled to the interlock member 25, such that the flap member 57 is locked in the closed position when the nosepiece unit 5 is not fitted to the substance-supply unit 11 and is free to be moved to the open position when the nosepiece unit 5 is fitted to the substance-supply unit 11, as will be described in more detail hereinbelow.

In this embodiment the rupturing mechanism 23 comprises an actuating member 73, here in the form of a button, which is configured to be depressed by the subject, a piercing element 75, here including two pins, which is supported by the actuating member 73 and operable to pierce the container C, and thereby provide for release of the contained powdered substance on the generation of a flow through the cavity 31 of the body section 21, and a biasing element 76, here a resilient element, such as a compression spring, for biasing the actuating member 73 to an inoperative position.

The actuating member 73 includes at least one guide element 77, here a pair of guide elements 77 in the form of arms, which are slideably disposed in the slots 43 of the first guide 41 of the body section 21. In this embodiment the at least one guide element 77 includes a detent 79, which retains the actuating member 73 captive in the first guide 41.

Figure 3:
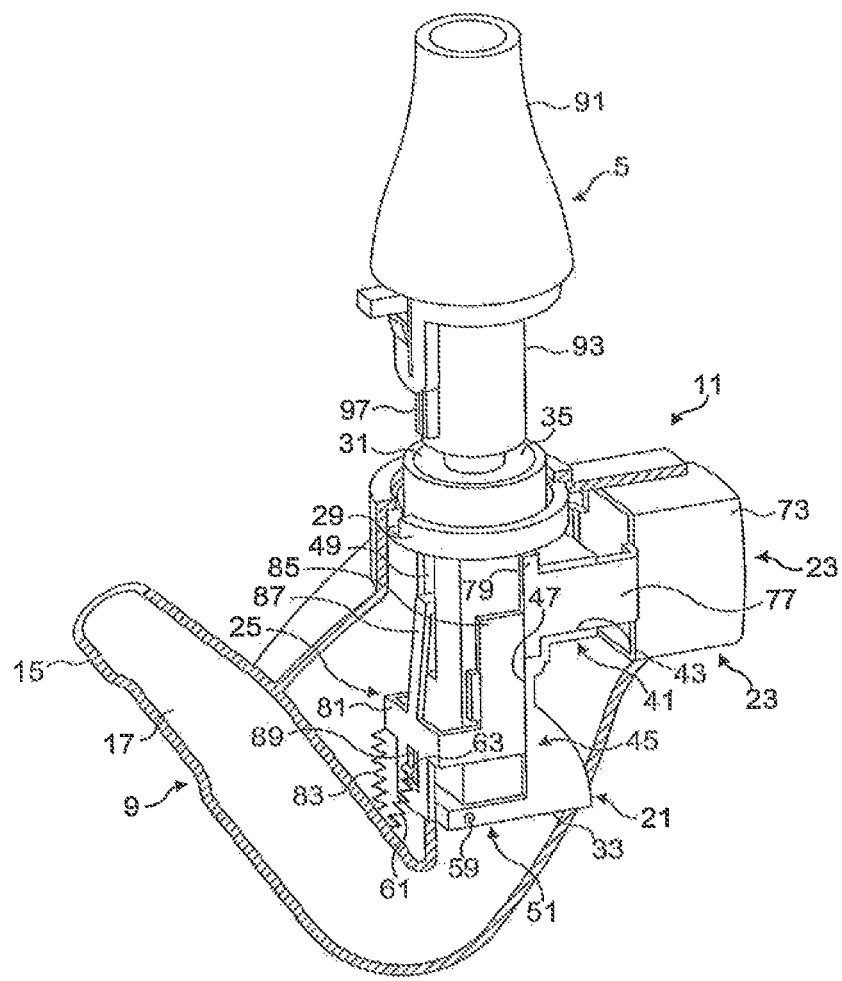
FIG. 3 illustrates a fragmentary perspective view of the delivery device of FIG. 1, prior to fitting of the nosepiece unit to the body assembly.

The interlock mechanism 25 comprises an interlock member 81 which is slideably disposed to the body section 21, in this embodiment longitudinally along the length thereof, and a biasing element 83, here a resilient element, such as a compression spring, for normally biasing the interlock member 81 to a locking position, as illustrated in FIG. 3, such as to prevent operation of the actuation mechanism 23 when the nosepiece unit 5 is not fitted to the substance-supply unit 11.

In this embodiment the interlock member 81 comprises at least one guide element 85, here a pair of guide elements 85 in the form of arms, which are slideably disposed in the slots 47 of the second guide 45 of the body section 21, a contact element 87, here an elongate element, which is slideably disposed in the slot 49 of the second guide 45 of the body section 21, and a locking element 89, here defined by an aperture, which is operative to engage with the locking element 63 on the flap member 57.

With this configuration, the interlock member 81, when biased to the locking position, as illustrated in FIG. 3, acts to lock the flap member 57 in the closed position by engagement of the locking element 89 of the interlock member 81 and the locking element 63 of the flap member 57, and the guide elements 85 of the interlock member 81 are located such as to prevent movement of the guide elements 77 of the actuating member 73, and thereby prevent actuation of the same, and, when the nosepiece unit 5 is fitted to the substance-supply unit 11, as will be described in more detail hereinbelow, the interlock member 81 is moved against the bias of the biasing element 83 to a released position, in which the locking element 89 of the interlock member 81 is disengaged from the locking element 63 of the flap member 57, such as to allow for the flap member 57 to be moved and opened on exhalation by the subject through the mouthpiece unit 9 at a predetermined flow rate, and the guide elements 85 of the interlock member 81 are moved clear of the guide elements 77 of the actuating member 73, such as to allow for actuation of the actuating member 73.

In one embodiment the mouthpiece unit 9 could include a heat exchanger which is in fluid communication with the mouthpiece 15 and acts to draw heat from the exhaled air flow as delivered through the mouthpiece 15, thus decreasing the temperature of the air flow as delivered to the cavity 31. By decreasing the temperature of the air flow, the humidity of the air flow is reduced, with the water vapor condensing in the heat exchanger, and the impact of condensation is significantly reduced, thus allowing for successive doses of powdered substance to be delivered without affecting the release of powdered substance from the containers C.

The nosepiece unit 5 comprises a nosepiece 91, in this embodiment a frusto-conical section, which is inserted into a nostril of the subject, in this embodiment to provide a sealing fit therewith, and a container chamber 93 which is in fluid communication with the nosepiece 91 and contains a container C containing a powdered substance for delivery to the nasal cavity of the subject.

In this embodiment the nosepiece unit 5 further comprises a grid, here a gauze, which is disposed between the nosepiece 91 and the container chamber 93, such as to prevent the container C or any parts thereof, such as resulting from rupturing of the container C, from passing through the nosepiece 91 and entering the nasal cavity of the subject.

In this embodiment the container chamber 93 and the grid, as components which contact the container C and the contained powder, are fabricated from a material having a low moisture sensitivity, here a plastics material, such as to reduce any tendency to become tacky in the presence of moisture, and therefore reduce the tendency for the container C and the powdered substance as contained thereby to adhere to the wall of the container chamber 93 or the grid.

In this embodiment the nosepiece 91, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 91.

In one embodiment the container C is a gelatine capsule.

In another embodiment the container C can be manufactured from a material which has a reduced tendency to become tacky in the presence of moisture, as occurs with gelatine capsules, and therefore reduce the tendency for the container C to adhere to the wall of the container chamber 93 or the grid.

In one embodiment the container C is formed of a cellulose derivative, such as hydroxypropyl methylcellulose (HPMC), hydroxypropylcellulose, methylcellulose, ethylcellulose and carboxymethylcellulose In another embodiment the container C can comprise a plastics material, preferably a water insoluble material, such as a polycarbonate.

In one embodiment the container C can be manufactured from a lightweight material, such as thin-wall section polymeric materials, which reduces the energy required to move the container C, typically by one or both of vibration and rotation, and thereby allow the delivery device to be operated at reduced flow rates, which is particularly advantageous for nasal delivery.

In an alternative embodiment the container C can include an outer coating of a material, such as parylene, which has a reduced tendency to become tacky in the presence of moisture, as occurs with gelatine capsules, and therefore reduce the tendency for the container C to adhere to the wall of the container chamber 93 or the grid.

In this embodiment, the container C is cylindrical in shape with hemispherical ends.

In other embodiments the container C could have other geometric forms, such as spherical, which allows for efficient powder release at low flow rates.

The nosepiece unit 5 further comprises a contact element 97, in this embodiment an axially-extending element, which is configured to be a sliding fit in the third slot 49 of the second guide 45 of the body section 21 of the substance-supply unit 11, such that, on inserting the nosepiece unit 5 into the body section 21, the contact element 97 engages the contact element 87 of the interlock member 81, in this embodiment the distal end thereof, such as to move the interlock member 81 to the released position.

Operation of the delivery device will now be described hereinbelow.

A subject first inserts a nosepiece unit 5 into the body section 21 of the substance-supply unit 11. On inserting the nosepiece unit 5 into the body section 21, the contact element 97 thereof engages the contact element 87 of the interlock member 81, such as to move the interlock member 81 to the released position when the nosepiece unit 5 is fully inserted into the substance-supply unit 11. With the interlock member 81 in the released position, the flap member 57 is disengaged from the locking element 89 of the interlock member 81 and free to be moved by an exhalation air flow, and the actuating member 73 of the rupturing mechanism 23 is operable by the subject.

The subject then operates the rupturing mechanism 23 to rupture the container C as contained in the container chamber 93 of the nosepiece unit 5.

The subject then inserts the nosepiece 91 into one of his/her nostrils, grips the mouthpiece 15 in his/her mouth, and exhales through the mouthpiece 15.

The exhaled air flow, where having a sufficient flow rate, is then driven through the cavity 31 of the body section 21 and the container chamber 93, which acts to move the container C, in this embodiment by vibration and rotation, and entrain the powdered substance as contained by the container C.

The exhaled air flow, as then entraining the powdered substance, is delivered though the nosepiece 91 into one nasal cavity of the subject.

In this embodiment the exhaled air flow is such as to pass around the posterior region of the nasal septum, and into the other nasal cavity, thereby achieving a bi-directional air flow as described in the applicants' earlier WO-A-00/051672.

Following use, the nosepiece unit 5 is then removed and the above-described procedure can be repeated with another nosepiece unit 5.

FIGS. 7 to 13 illustrate a delivery device in accordance with a second embodiment of the present invention.

The delivery device comprises a housing 103, a nosepiece unit 105, a mouthpiece unit 109 and a substance-supply unit 111 which is fluidly connected to the nosepiece and mouthpiece units 105, 109. As will be described in more detail hereinbelow, the delivery device is a re-usable device, to which containers C, in this embodiment capsules, containing substance to be delivered to the nasal cavity of a subject are removably loaded.

As illustrated in FIGS. 12 and 13, the containers C comprise first and second body parts 115, 117, which together define an enclosed chamber 119 and are movably disposed, here slideably disposed relative to one another. The body parts 115, 117 each include at least one aperture 121, 123, in this embodiment a plurality of apertures 121, 123, which are dosed with the body parts 115, 117 in a first, dosed configuration and are opened by sliding of the body parts 115, 117 to a second, open configuration in which the apertures 121, 123 in the body parts 115, 117 are aligned.

In this embodiment the body parts 115, 117 include inter-engaging guides 125, 127, which provide for axial sliding of the body parts 115, 117 without any rotation thereof, thereby ensuring alignment of the apertures 121, 123.

In this embodiment the housing 103 comprises a body 135 to which the nosepiece unit 105, the mouthpiece unit 109 and the substance-supply unit 111 are disposed, and a cover 137, here a hinged lid, which is operable between a closed position in which the nosepiece and mouthpiece units 105, 109 are enclosed and an open position in which the nosepiece and mouthpiece units 105, 109 are exposed for use.

The body 135 includes a container aperture 139, in this embodiment an elongate aperture, through which a container C is loaded and removed from the substance-supply unit 111, as will be described in more detail hereinbelow.

The nosepiece unit 105 comprises a nosepiece 141, in this embodiment a frusto-conical section, which is inserted into a nostril of the subject, here to provide a sealing fit therewith, and a flow channel 143 which is fluidly connected to the nosepiece 141 and includes a grid 145, in this embodiment a gauze, at one, lower end thereof.

The mouthpiece unit 109 comprises a mouthpiece 147 which in use is gripped in the lips of a subject, and a one-way, non-return valve 149 which is fluidly connected to the mouthpiece 147 and is operative to prevent inhalation by the subject through the mouthpiece 147.

The substance-supply unit 111 comprises a support member 151 which is fixed to the body 135 of the housing 103, and a body section 153 which is movably disposed, in this embodiment rotatably disposed, to the support member 151.

The support member 151 includes a cam member 161 which includes a cam track 163 which extends between first and second positions 165, 167 and includes stops 169 at the respective ends thereof, in this embodiment at angular positions of 180 degrees. In this embodiment the cam track 163 includes a first cam section, corresponding to a first phase of rotation, which is inclined from a first, lower position 165 to the second, higher position 167 and a second cam section, corresponding to a second phase of rotation, which is inclined from the second, higher position 167 to the first, lower position 165.

The body section 153 comprises a body member 171, in this embodiment a tubular member, which defines a container chamber 172 and includes a first, container-receiving aperture 173 in the lateral wall thereof for receiving a container C, a second, inlet flow aperture 175 at one, the lower, end thereof, and a third, outlet flow aperture 177 at the other, upper, end thereof which receives the flow channel 143 of the nosepiece unit 105 and is slideably disposed thereto. As will be described in more detail hereinbelow, the body section 153 is rotatable between a first, dosed position in which the container-receiving aperture 173 is closed by the enclosure member of the body 135 and the inlet aperture 175 is in fluid communication with the mouthpiece unit 109, and a second, open position in which the container-receiving aperture 173 is open to the container aperture 139 in the body 135 and the inlet aperture 175 is closed.

The body section 153 further comprises a grid 181, here a gauze, which is located within the body member 171 at a location intermediate the container-receiving aperture 173 and the inlet flow aperture 175, which acts to support a container C when loaded into the body member 171. As will be described in more detail hereinbelow, the grid 181 is configured to compress the container C against the grid 145 in the nosepiece unit 105, such as to open the container C by aligning the apertures 121, 123 thereof.

The body section 153 further comprises a cam follower 179, in this embodiment in the form of a projection which projects laterally from the body member 171, which is configured to ride on the cam track 163 of the cam member 161 and provide for axial displacement of the body section 153 relative to the support member 151 on rotation of the body section 153.

Figure 7:
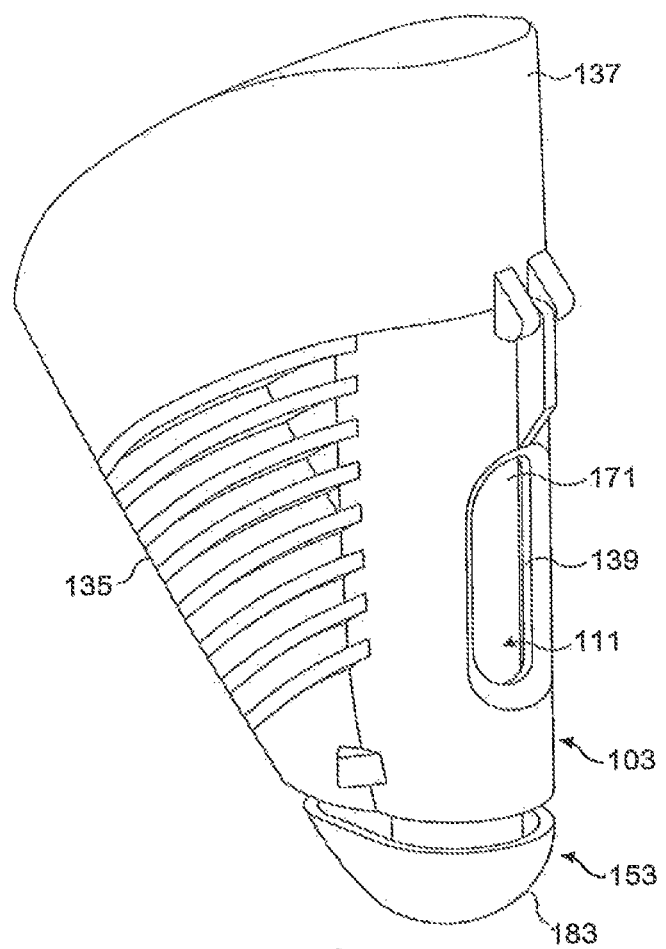
FIG. 7 illustrates a perspective view of a delivery device in accordance with a second embodiment of the present invention.
Figure 8:
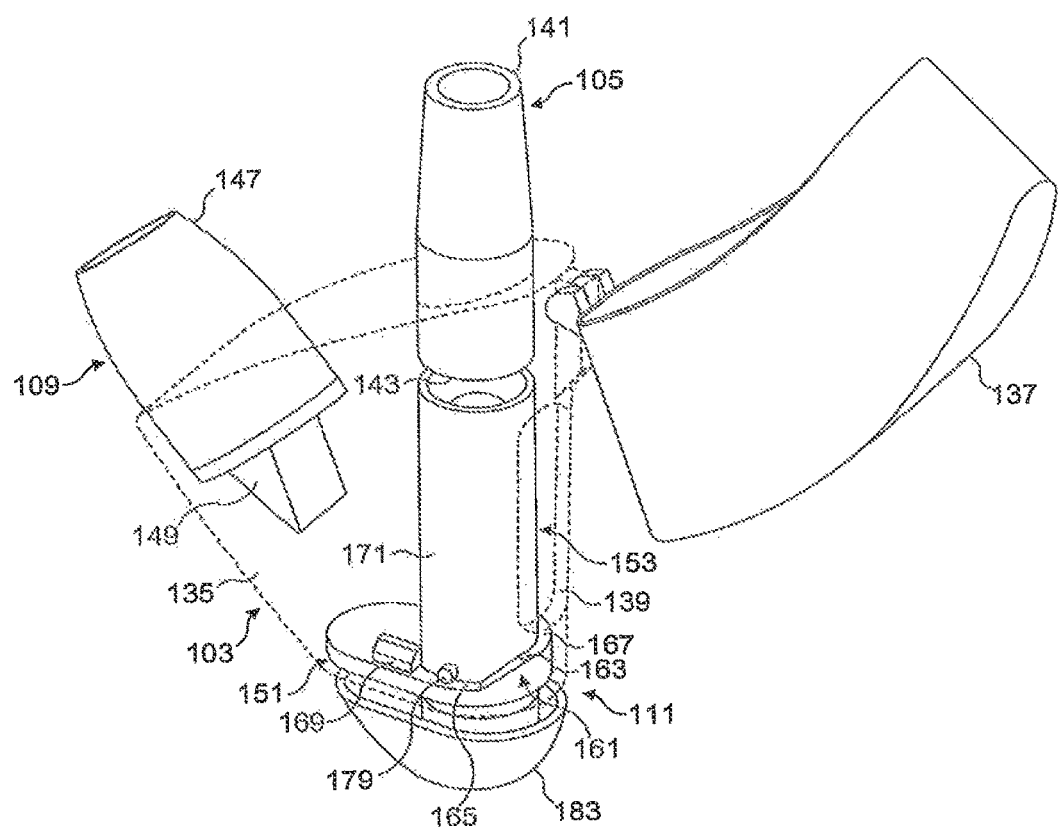
FIG. 8 illustrates a part cut-away perspective view from the rear and one side of the delivery device of FIG. 7, with the cover in an open position.
Figure 9:
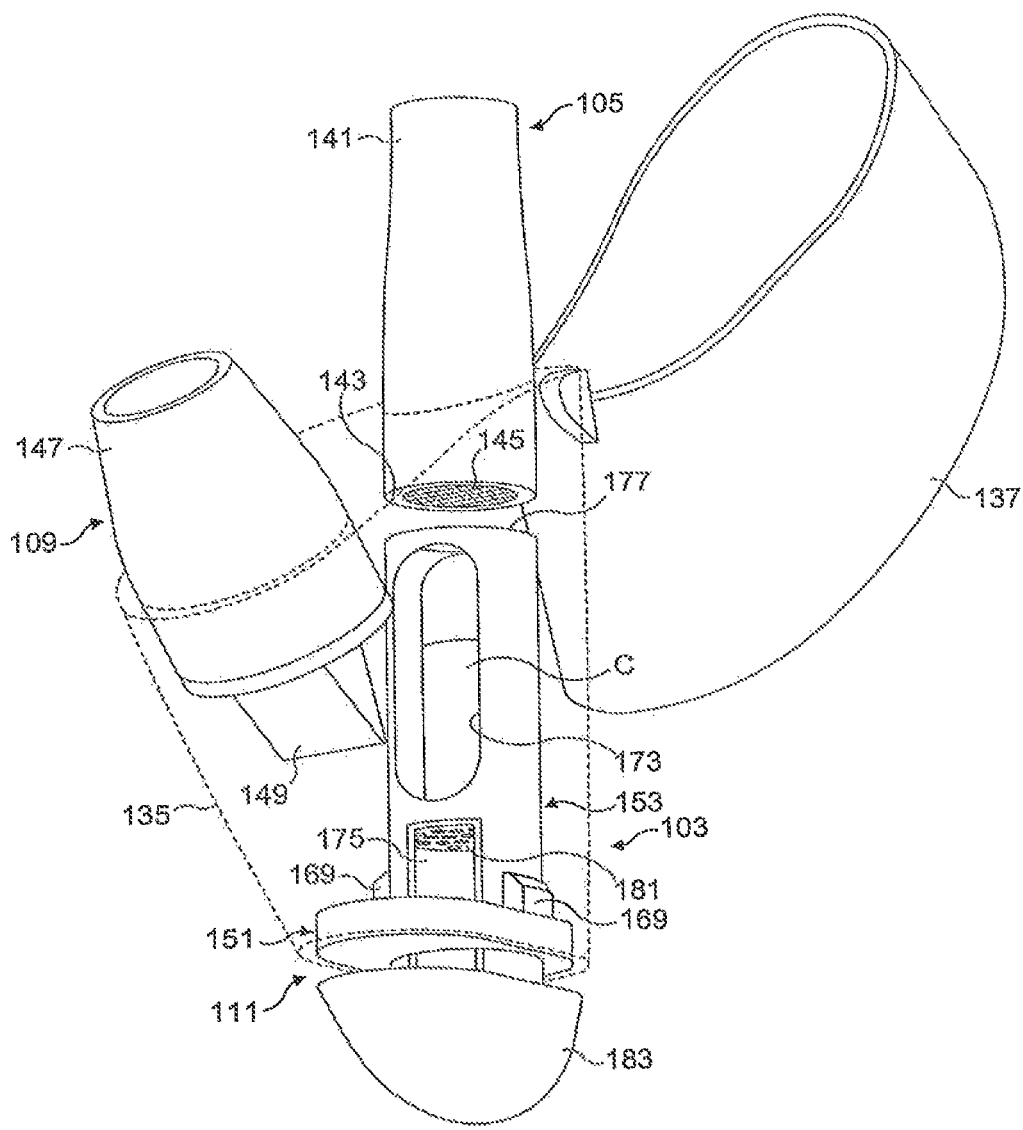
FIG. 9 illustrates a part cut-away perspective view from the front and one side of the delivery device of FIG. 7, with the cover in an open position.
Figure 10:
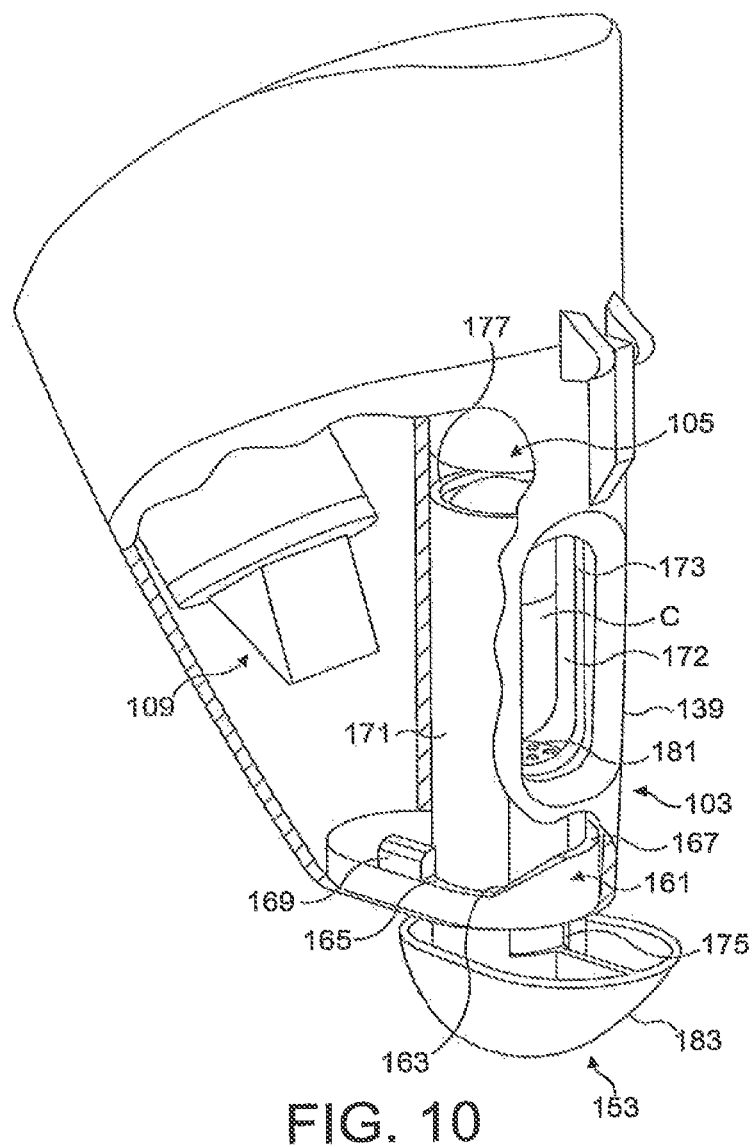
FIG. 10 illustrates a part cut-away perspective view from the rear and one side of the delivery device of FIG. 7, with the container chamber in the open position.
Figure 11:
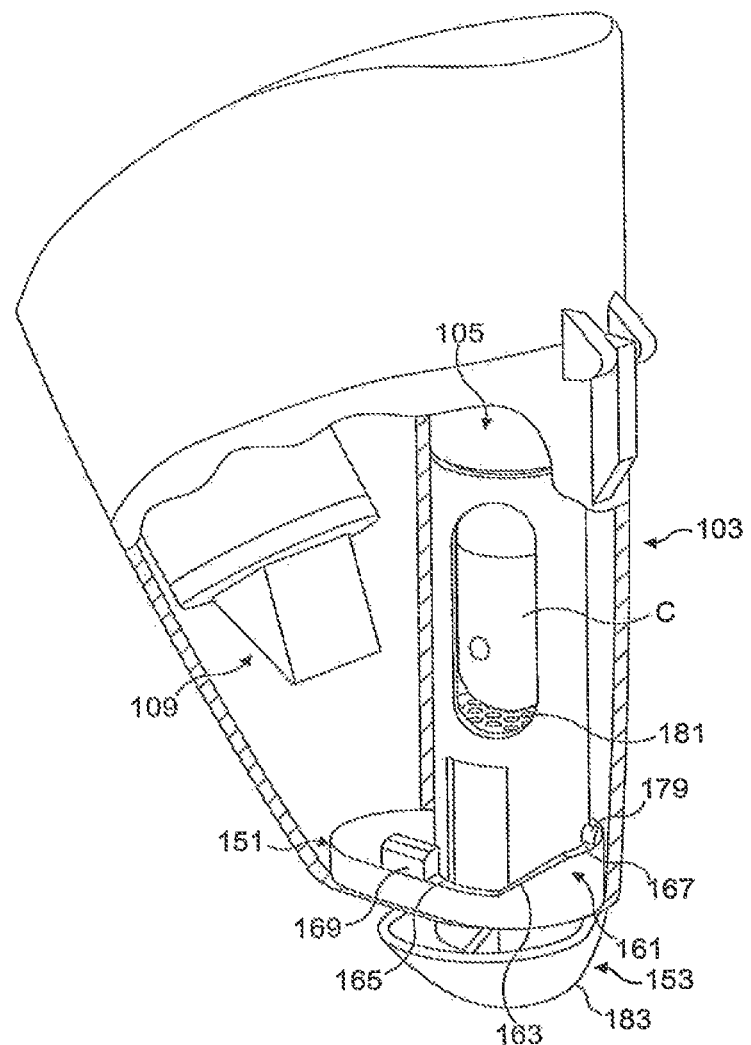
FIG. 11 illustrates a part cut-away perspective view from the rear and one side of the delivery device of FIG. 7, with the container chamber in the intermediate position.
Figure 12:
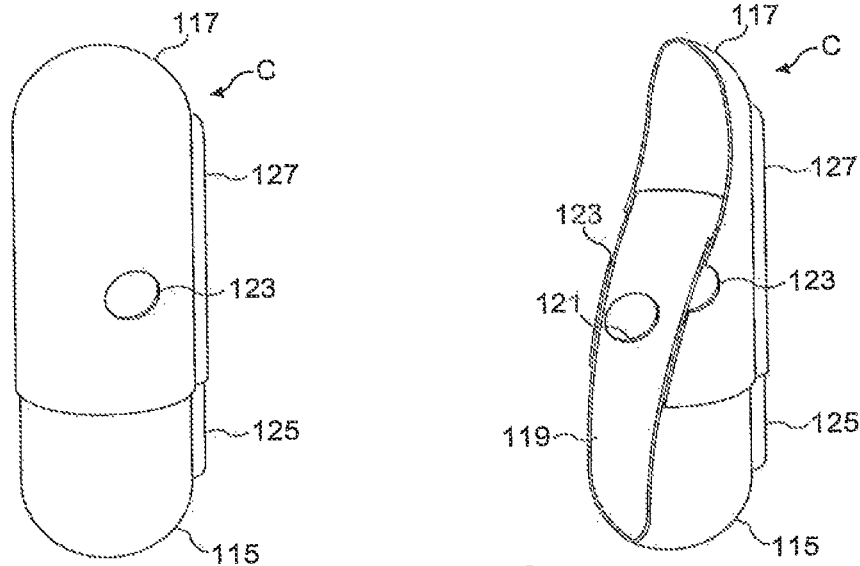
FIG. 12 illustrates a container in accordance with one embodiment of the present invention, in the closed configuration.
Figure 13:
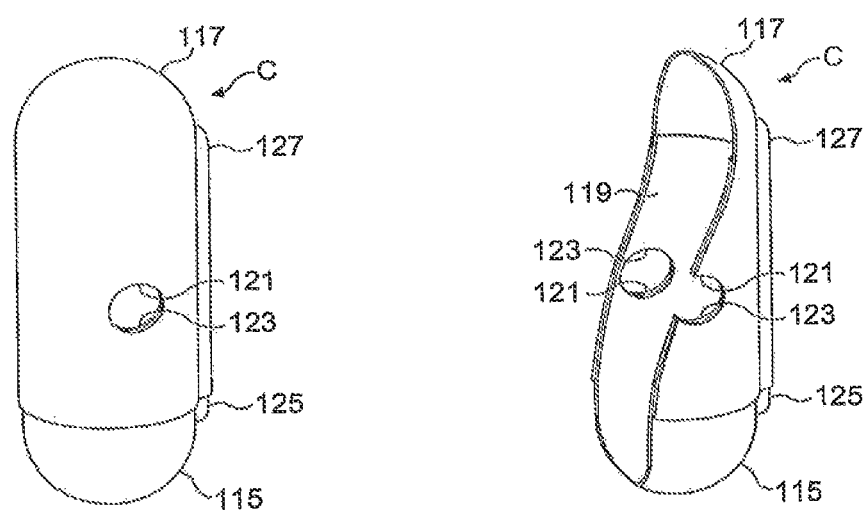
FIG. 13 illustrates the container of FIG. 12 in the open configuration.

In this embodiment the body section 153 is rotatable between a closed position, as illustrated in FIGS. 7 to 9, in which the cam follower 179 is located on the cam track 163 of the cam member 161 at the first, lower position 165, through an intermediate position, as illustrated in FIG. 11, in which the cam follower 179 is located on the cam track 163 of the cam member 161 at the second, raised height 167, and to an open position, as illustrated in FIG. 10, in which the cam follower 179 is located on the cam track 163 of the cam member 161 at the first height 165. When the cam follower 179 is located on the cam track 163 of the cam member 161 at the first height 165, the grid 181 of the body section 153 is spaced from the grid 145 of the nosepiece unit 105, such as to allow for axial movement and rotation of a contained container C, and, when the cam follower 179 is located on the cam track 163 of the cam member 161 at the second height 167, the grid 181 of the body section 153 is spaced more closely to the grid 145 of the nosepiece unit 105, such as to cause the compression of the body parts 115, 117 of the container C and thereby open the container C.

The body section 153 further comprises an actuating member 183, in this embodiment in the form of a knob, which can be gripped by the subject and is connected to the body member 171, in this embodiment at a lower end thereof, such as to provide for rotation of the body member 171.

In one embodiment the mouthpiece unit 109 could include a heat exchanger which is in fluid communication with the mouthpiece 147 and acts to draw heat from the exhaled air flow as delivered through the mouthpiece 147, thus decreasing the temperature of the delivered air flow. By decreasing the temperature of the air flow, the humidity of the air flow is reduced, with the water vapor condensing in the heat exchanger, and the impact of condensation is significantly reduced, thus allowing for successive doses of powdered substance to be delivered without affecting the release of powdered substance from the containers C.

In this embodiment the container chamber 172 and the grids 145, 181, as components which contact the container C and the contained powder, are fabricated from a material having a low moisture sensitivity, here a plastics material, such as to reduce any tendency to become tacky in the presence of moisture, and therefore reduce the tendency for the container C and the powdered substance as contained thereby to adhere to the wall of the container chamber 172 or the grids 145, 181.

In this embodiment the nosepiece 141, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 141.

In one embodiment the container C is a gelatine capsule.

In another embodiment the container C can be manufactured from a material which has a reduced tendency to become tacky in the presence of moisture, as occurs with gelatine capsules, and therefore reduce the tendency for the container C to adhere to the wall of the container chamber 172 or the grids 145, 181.

In one embodiment the container C is formed of a cellulose derivative, such as hydroxypropyl methylcellulose (HPMC), hydroxypropylcellulose, methylcellulose, ethylcellulose and carboxymethylcellulose In another embodiment the container C can comprise a plastics material, preferably a water insoluble material, such as a polycarbonate.

In one embodiment the container C can be manufactured from a lightweight material, such as thin-wall section polymeric materials, which reduces the energy required to move the container C, typically by one or both of vibration and rotation, and thereby allow the delivery device to be operated at reduced flow rates, which is particularly advantageous for nasal delivery.

In an alternative embodiment the container C can include an outer coating of a material, such as parylene, which has a reduced tendency to become tacky in the presence of moisture, as occurs with gelatine capsules, and therefore reduce the tendency for the container C to adhere to the wall of the container chamber 172 or the grids 145, 181.

In this embodiment, the container C is cylindrical in shape with hemispherical ends.

In other embodiments the container C could have other geometric forms, such as spherical, which allows for efficient powder release at low flow rates.

Operation of the delivery device will now be described hereinbelow.

A subject first operates the actuating member 183 such as to rotate the body section 153 from the closed position, as illustrated in FIGS. 7 to 9, in this embodiment through 180 degrees, to the open position, as illustrated in FIG. 10, in which the container aperture 173 in the body member 171 is aligned with the container aperture 139 in the housing 103, such as to allow a container C to be loaded into the container chamber 172 of the body member 171.

The subject then again operates the actuating member 183 such as to return the body section 153 to the dosed position. In so operating the actuating member 183, the body section 153 is first moved from the open position in which the cam follower 179 on the body section 153 is located on the cam track 163 of the cam member 161 at the first, lower height 165, through an intermediate position, as illustrated in FIG. 11, in which the cam follower 179 is located on the cam track 163 of the cam member 161 at the second, raised height 167. In this intermediate position, the grid 181 of the body section 153 is spaced more closely to the grid 145 of the nosepiece unit 105, such as to cause the compression of the body parts 115, 117 of the container C and thereby open the container C. With continued operation of the actuating member 183, the body section 153 is moved from the intermediate position to the dosed position, as illustrated in FIGS. 7 to 9, in which the cam follower 179 is located on the cam track 163 of the cam member 161 at the first, lower height 165 and the grid 181 of the body section 153 is spaced further apart from the grid 145 of the nosepiece unit 105, such as to allow for axial movement and rotation of a contained container C, the container aperture 173 in the body member 171 is closed by the enclosure member of the housing 103 and the inlet aperture 175 is in fluid communication with the mouthpiece unit 109.

The subject then inserts the nosepiece 141 into one of his/her nostrils, grips the mouthpiece 147 in his/her mouth, and exhales through the mouthpiece 147.

The exhaled air flow, where having a sufficient flow rate, is then driven through the container chamber 172 of the body member 171 of the body section 153, which acts to move the container C, in this embodiment by vibration and rotation, and entrain the powdered substance as contained by the container C.

The exhaled air flow, as then entraining the powdered substance, is delivered though the nosepiece 141 into one nasal cavity of the subject.

In this embodiment the exhaled air flow has such a pressure as to pass around the posterior region of the nasal septum, and into the other nasal cavity, thereby achieving a bi-directional air flow as described in the applicants' earlier WO-A-00/051672.

Following use of the device, the actuating member 183 is first operated such as to rotate the body section 153 from the closed position, in this embodiment through 180 degrees, to the open position, in which the container aperture 173 in the body member 171 is aligned with the container aperture 139 in the housing 103, such as to allow the used container C to be removed from the container chamber 172 of the body member 171, and the actuating member 183 is subsequently operated such as to rotate the body section 153 from the open position, in this embodiment through 180 degrees, to the closed position, in which the container aperture 173 in the body member 171 is closed.

FIGS. 14 to 17 illustrate a delivery device in accordance with a third embodiment of the present invention.

The delivery device comprises a housing 203, a nosepiece unit 205, a mouthpiece unit 209 and a substance-supply unit 211 which is fluidly connected to the nosepiece and mouthpiece units 205, 209. As will be described in more detail hereinbelow, the delivery device is a re-usable device, to which containers C, in this embodiment capsules, containing substance to be delivered to the nasal cavity of a subject are removably loaded.

Figure 14:
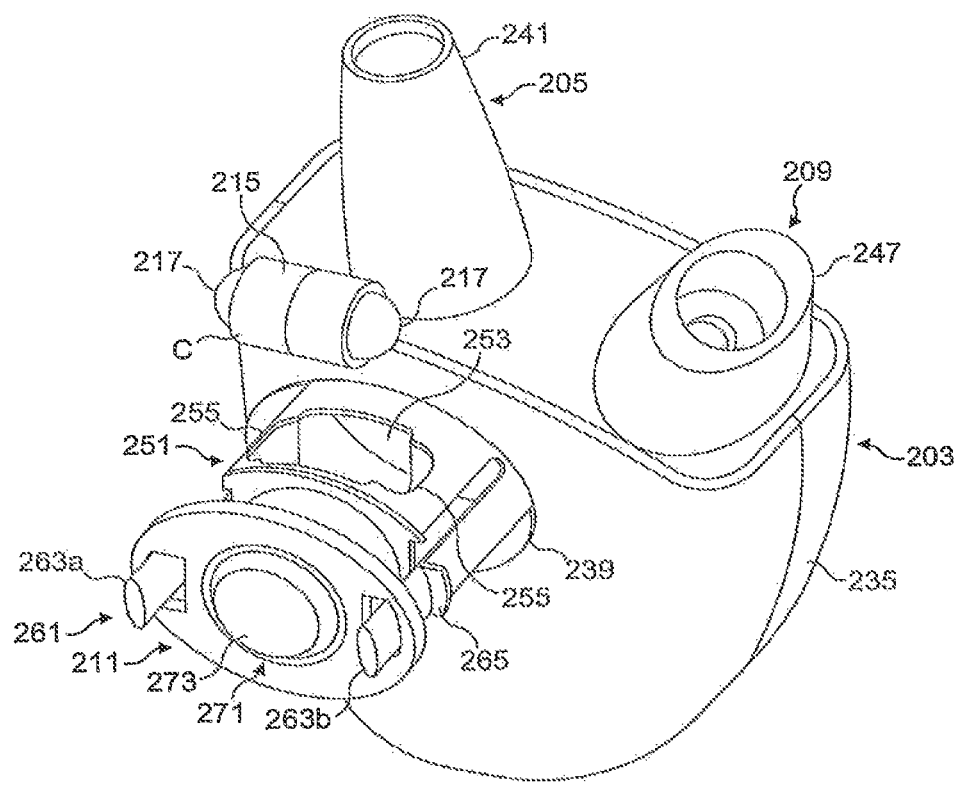
FIG. 14 illustrates a perspective view of a delivery device in accordance with a third embodiment of the present invention, with the substance-supply unit in the open position for receiving a container.
Figure 15:
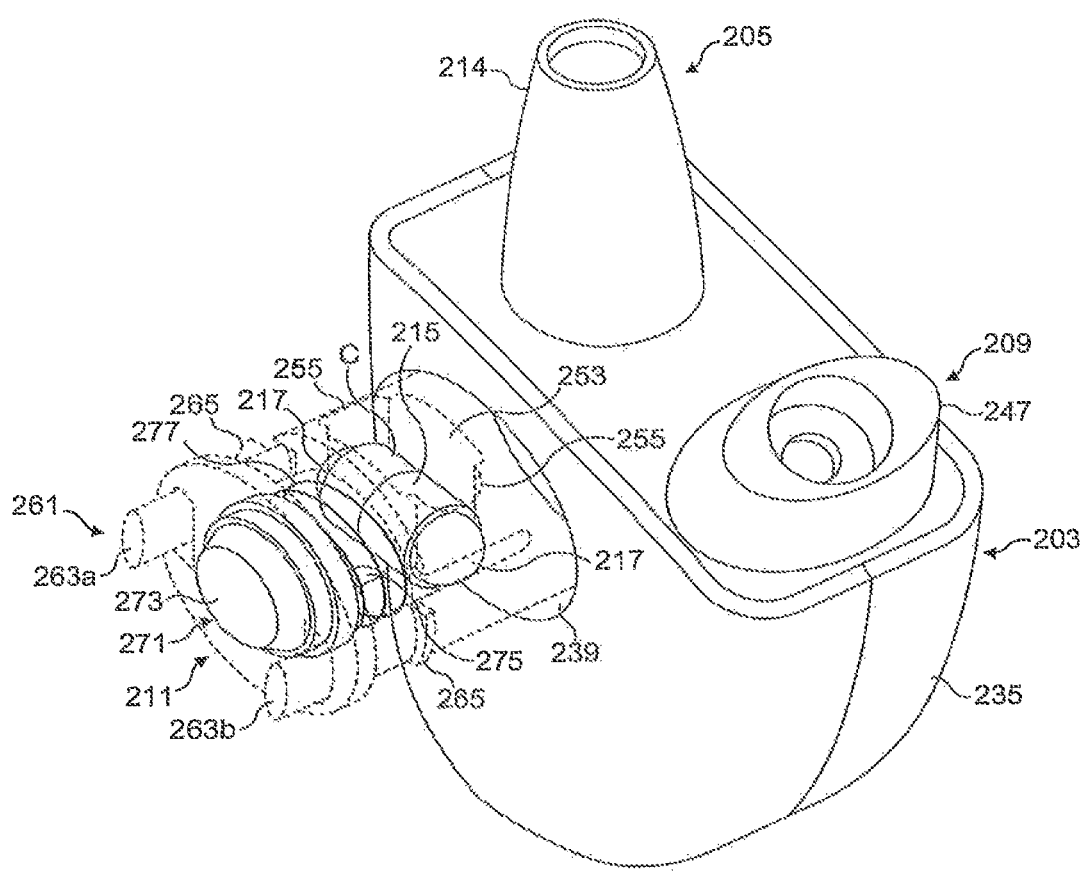
FIG. 15 illustrates the perspective view of FIG. 14, where partially cut-away and with the substance-supply unit loaded with a container.

As illustrated in FIGS. 14 and 15, the containers C comprise a main body part 215, in this embodiment of cylindrical section, and first and second supports 217 at the respective ends of the body part 215, which act as bearings about which the container C is rotated. In this embodiment the supports 217 comprise hemi-spherical structures, which are of smaller radial dimension than the body part 215 and located on the longitudinal axis of the body part 215. In one embodiment the supports 217 could be offset relative to one another or eccentrically weighted, such as to promote the vibration of the container C on rotation.

In this embodiment the housing 203 comprises a body 235 to which the nosepiece unit 205, the mouthpiece unit 209 and the substance-supply unit 211 are disposed.

The body 235 includes a container aperture 239, through which a container C is loaded and removed from the substance-supply unit 211, as will be described in more detail hereinbelow.

The nosepiece unit 205 comprises a nosepiece 241, in this embodiment as defined by a tubular section, which is inserted into a nostril of the subject, here to provide a sealing fit therewith.

In one embodiment the nosepiece unit 205 can include a grid, such as a gauze, for preventing the container C or parts thereof from passing through the nosepiece 241 and into the nasal cavity of the subject.

The mouthpiece unit 209 comprises a mouthpiece 247 which in use is gripped in the lips of a subject, and a heat exchanger 249 which is in fluid communication with the mouthpiece 247 and acts to draw heat from the exhaled air flow as delivered through the mouthpiece 247, thus decreasing the temperature of the delivered air flow. By decreasing the temperature of the air flow, the humidity of the air flow is reduced, with the water vapor condensing in the heat exchanger 249, and the impact of condensation is significantly reduced, thus allowing for successive doses of powdered substance to be delivered without affecting the release of powdered substance from the containers C.

In this embodiment the heat exchanger comprises a plurality of parallel, elongate tubes.

Figure 16:
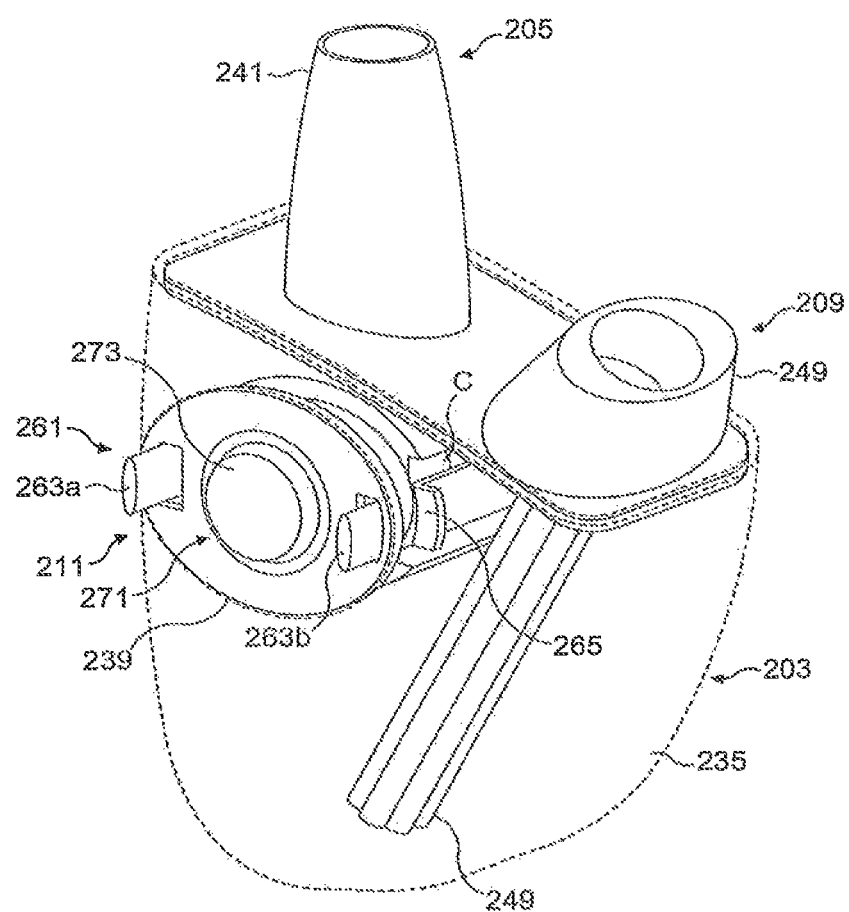
FIG. 16 illustrates a perspective view of the delivery device of FIG. 14, where partially cut-away and with the substance-supply unit loaded with a container.
Figure 17:
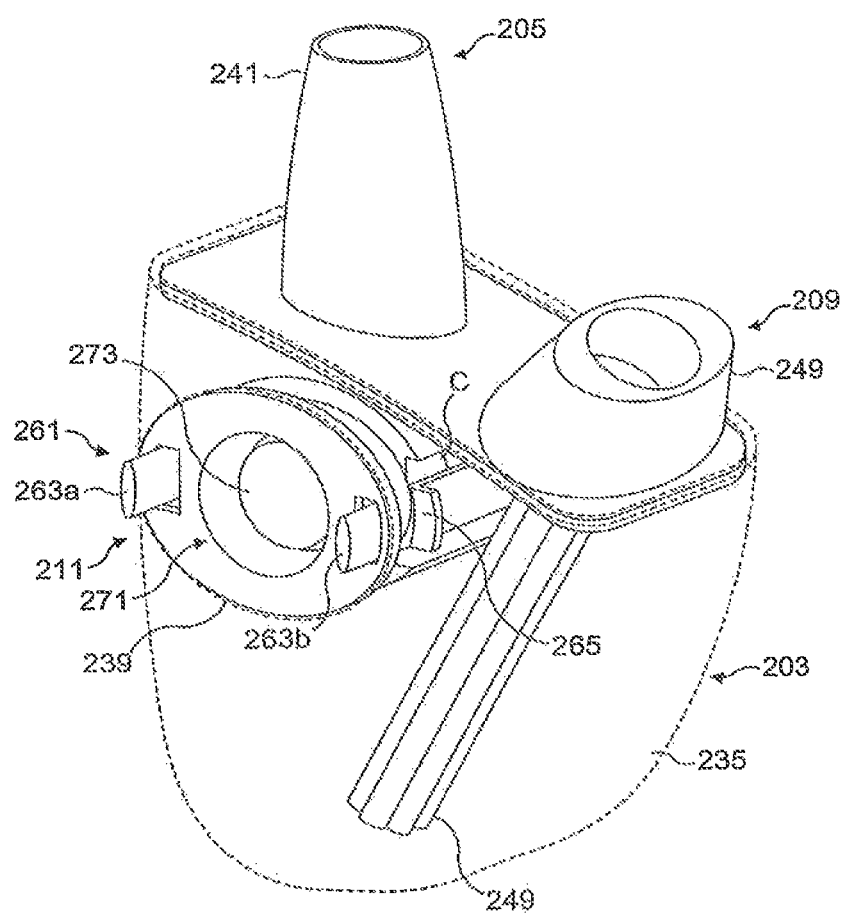
FIG. 17 illustrates a perspective view of the delivery device of FIG. 14, where partially cut-away and with the substance-supply unit loaded with a container and the actuating member of the rupturing mechanism in the depressed position.
Figure 18:
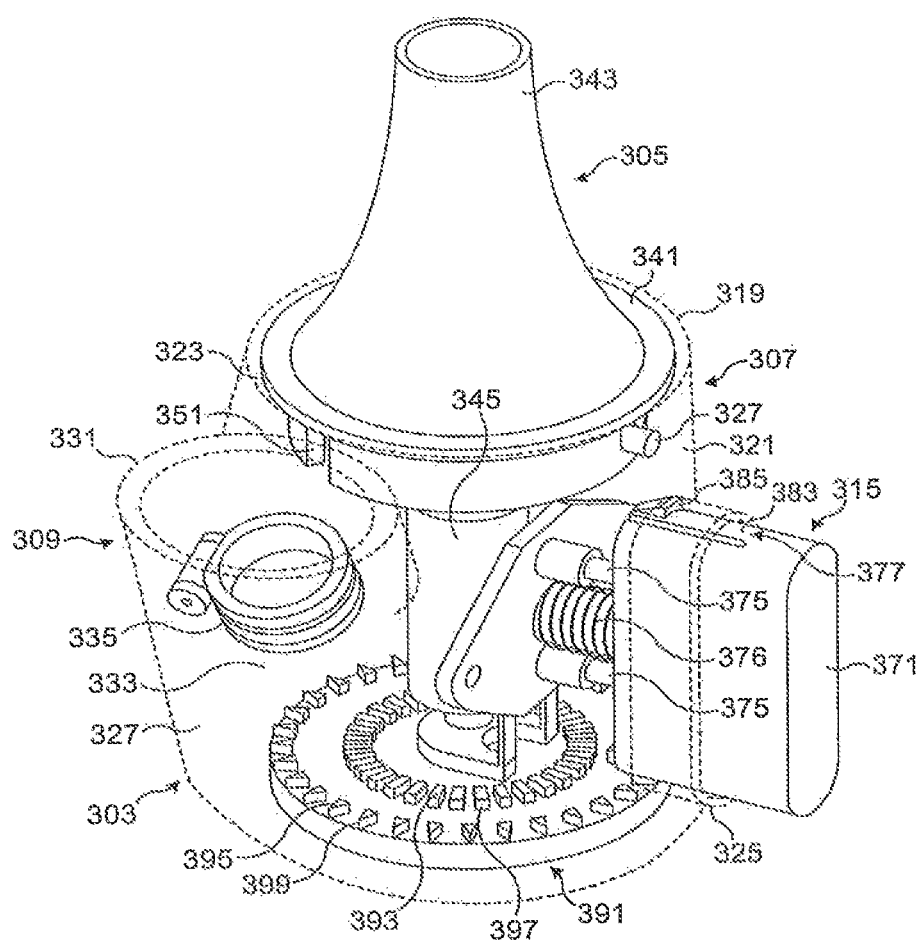
FIG. 18 illustrates a part cut-away perspective view of a delivery device in accordance with a fourth embodiment of the present invention.
Figure 19:
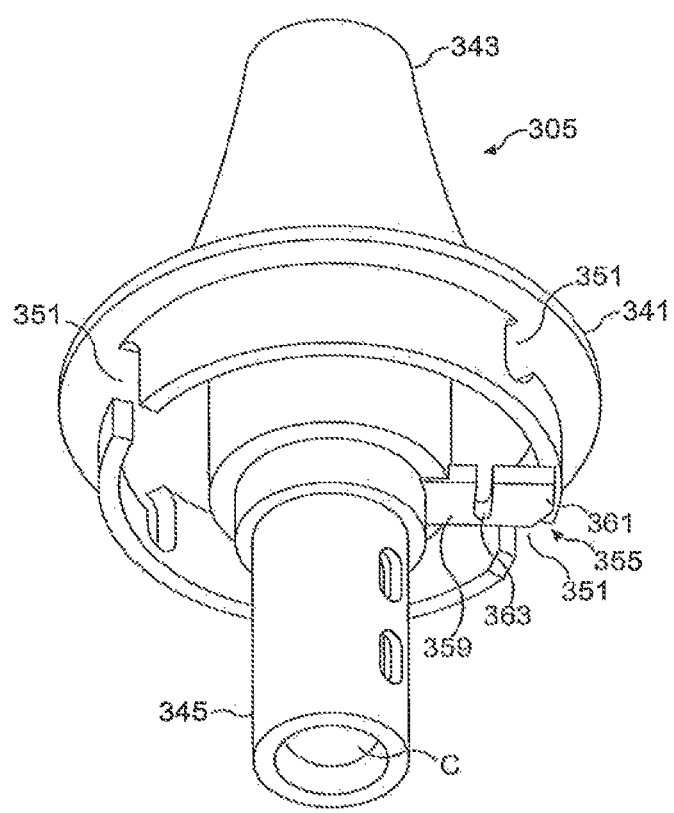
FIG. 19 illustrates a perspective view of the nosepiece unit of the delivery device of FIG. 18.

The substance-supply unit 211 comprises a container-receiving member 251, which is slideably disposed within the container aperture 239 in the housing 203 between an open position for enabling the loading of a container C thereinto, as illustrated in FIGS. 14 and 15, and a closed position, as illustrated in FIGS. 16 and 17, in which the container C is contained within the housing 203.

In this embodiment the container-receiving member 251 comprises a cavity 253 which defines an air flow channel from the mouthpiece 245 to the nosepiece 241 and includes first and second supports 255, in this embodiment part-spherical structures which act as bearings and are configured to receive the respective supports 217 of the container C, such that, on delivery of an exhalation air flow through the cavity 253, the container C is rotated by the supports 217 thereof.

The substance-supply unit 211 further comprises a locking mechanism 261 which is operative to lock the substance-supply unit 211 in the closed position.

In this embodiment the locking mechanism 261 comprises at least one arm member 263, in this embodiment a plurality of arm members 263a, 263b, which are deflectable, here inwardly, and each include a detent 265 which is engageable with a surface of the housing 203, such as to lock the substance-supply unit 211 in the closed position. In this embodiment the substance-supply unit 211 is located in the locked position by pushing the substance-supply unit 211 into the housing 203, which causes the detents 265 on the arm members 263a, 263b to ride over the housing 203 and be locked behind a surface thereof, and withdrawn from the housing 203 by deflecting the arm members 263a, 263b, here by squeezing the arm members 263a, 263b inwardly, such as to release the detents 265 from engagement with the respective surfaces of the housing 203, and pulling the substance-supply unit 211 outwardly.

The substance-supply unit 211 further comprises a rupturing mechanism 271 which is operable to rupture the container C as contained by the nosepiece unit 205.

In this embodiment the rupturing mechanism 271 comprises an actuating member 273, here in the form of a button, which is configured to be depressed by the subject, as illustrated in FIG. 17, a piercing element 275, here including two pins, which is supported by the actuating member 273 and operable to drive the piercing element 275 to pierce the container C, and thereby provide for release of the contained powdered substance on the generation of a flow through the cavity 253 in the container-receiving member 251, and a resilient element 277, here a compression spring, for returning the actuating member 273 to the rest position following piercing of the container C.

In this embodiment the container-receiving member 251 and the grid, as components which contact the container C and the contained powder, are fabricated from a material having a low moisture sensitivity, here a plastics material, such as to reduce any tendency to become tacky in the presence of moisture, and therefore reduce the tendency for the container C and the powdered substance as contained thereby to adhere to the container-receiving member 251 or the grid.

In this embodiment the nosepiece 241, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 241.

In one embodiment the container C is a gelatine capsule.

In another embodiment the container C can be manufactured from a material which has a reduced tendency to become tacky in the presence of moisture, as occurs with gelatine capsules, and therefore reduce the tendency for the container C to adhere to the container-receiving member 251 or the grid.

In one embodiment the container C is formed of a cellulose derivative, such as hydroxypropyl methylcellulose (HPMC), hydroxypropylcellulose, methylcellulose, ethylcellulose and carboxymethylcellulose In another embodiment the container C can comprise a plastics material, preferably a water insoluble material, such as a polycarbonate.

In one embodiment the container C can be manufactured from a lightweight material, such as thin-wall section polymeric materials, which reduces the energy required to move the container C, typically by one or both of vibration and rotation, and thereby allow the delivery device to be operated at reduced flow rates, which is particularly advantageous for nasal delivery.

In an alternative embodiment the container C can include an outer coating of a material, such as parylene, which has a reduced tendency to become tacky in the presence of moisture, as occurs with gelatine capsules, and therefore reduce the tendency for the container C to adhere to the container-receiving member 251 or the grid.

Operation of the delivery device will now be described hereinbelow.

A subject first withdraws the substance-supply unit 211 by deflecting the arm members 263a, 263b of the locking mechanism 261, here by squeezing the arm members 263a, 263b inwardly, such as to release the detents 265 thereof from engagement with the respective surfaces of the housing 203, and pulling the substance-supply unit 211 outwardly.

The subject then loads a container C into the cavity 253 in the container-receiving member 251, such that the end parts 217 of the container C are located on the respective supports 255 of the cavity 253. It will be appreciated that this design allows the containers C for different substances to be sized differently, such as to prevent the device from being used improperly with different substances.

The subject then closes the substance-supply unit 211 by pushing the substance-supply unit 211 into the housing 203, which causes the detents 265 on the arm members 263a, 263b to ride over the housing 203 and be locked behind a surface thereof.

The subject then operates the rupturing mechanism 271 to rupture the container C, in this embodiment by depressing the actuating member 273 thereof, as illustrated in FIG. 17, following which the actuating member 273 is returned to the rest position by the biasing element 277 thereof.

The subject then inserts the nosepiece 241 into one of his/her nostrils, grips the mouthpiece 247 in his/her mouth, and exhales through the mouthpiece 247.

The exhaled air flow, where having a sufficient flow rate, is then driven through the cavity 253 of the container-receiving member 251, which acts to move the container C, in this embodiment by vibration and rotation, and entrain the powdered substance as contained by the container C.

The exhaled air flow, as then entraining the powdered substance, is delivered though the nosepiece 241 into one nasal cavity of the subject.

In this embodiment the exhaled air flow has such a pressure as to pass around the posterior region of the nasal septum, and into the other nasal cavity, thereby achieving a bi-directional air flow as described in the applicants' earlier WO-A-00/051672.

Following use of the device, the substance-supply unit 211 is opened by deflecting the arm members 263a, 263b of the locking mechanism 261, here by squeezing the arm members 263a, 263b inwardly, such as to release the detents 265 thereof from engagement with the respective surfaces of the housing 203, and pulling the substance-supply unit 211 outwardly.

The subject then unloads the container C from the cavity 253 in the container-receiving member 251, and doses the substance-supply unit 211, in this embodiment by pushing the substance-supply unit 211 into the housing 203, which causes the detents 265 on the arm members 263a, 263b to ride over the housing 203 and be locked behind respective surfaces thereof.

FIGS. 18 to 26 illustrate a delivery device in accordance with a fourth embodiment of the present invention.

The delivery device comprises a main, body assembly 303 and a nosepiece unit 305, which contains a container C, in this embodiment a capsule, containing substance to be delivered to the nasal cavity of a subject and is removably fitted to the body assembly 303, such as to allow for the re-use of the device, as will be described in more detail hereinbelow.

The body assembly 303 comprises a housing 307, a mouthpiece unit 309, a rupturing mechanism 315 which is operable to rupture the container C as contained by the nosepiece unit 305, and a locking mechanism 317 for preventing operation of the rupturing mechanism 315 without a nosepiece unit 305 being fitted to the housing 307 and also after a predetermined number of operations.

The housing 307 comprises a body 319 which defines a cavity 321 and includes a first, fitting aperture 323 in which the nosepiece unit 305 is fitted and a second, clearance aperture 325 through which extends an actuating member 371 of the rupturing mechanism 315.

In this embodiment the body 319 includes at least one, here a plurality of projections 327 which are disposed about the fitting aperture 323, such as to provide for the screw-fitting of the nosepiece unit 305 to the housing 307.

The mouthpiece unit 309 comprises a mouthpiece 331 which in use is gripped in the lips of a subject, an air flow channel 333 which is fluidly connected to the cavity 321 of the housing 307, and a one-way, non-return valve 335 for preventing inhalation through the mouthpiece 331.

In this embodiment the housing 307 and the mouthpiece unit 309 are integrally formed, typically from a plastics material.

The nosepiece unit 305 comprises a body member 341 which is configured to fit in the fitting aperture 323 in the housing 307, a nosepiece 343, here as defined by a tubular section, which is supported by the body member 341 and is in use inserted into a nostril of the subject, here to provide a sealing fit therewith, and a container chamber 345 which is in fluid communication with the nosepiece 343 and contains a container C containing a powdered substance for delivery to the nasal cavity of the subject.

In this embodiment the body member 341 includes at least one, here a plurality of recesses 351 which are disposed thereabout in correspondence to the projections 327 which are disposed about the fitting aperture 323 of the housing 307, such as to provide for the screw-fitting of the nosepiece unit 305 to the housing 307. With this configuration, fitting of the nosepiece unit 305 to the housing 307 first requires insertion of the nosepiece unit 305 into the housing 307 and subsequently rotation of the nosepiece unit 305 in one sense, here in a counter-clockwise sense when viewed from above.

The nosepiece unit 305 further comprises a release member 355 which is configured to engage a counterpart latch member 377 on the actuating member 371 of the rupturing mechanism 315, such as to release the actuating member 371 to an operative position following fitting of the nosepiece unit 305, as will be described in more detail hereinbelow.

Figure 20:
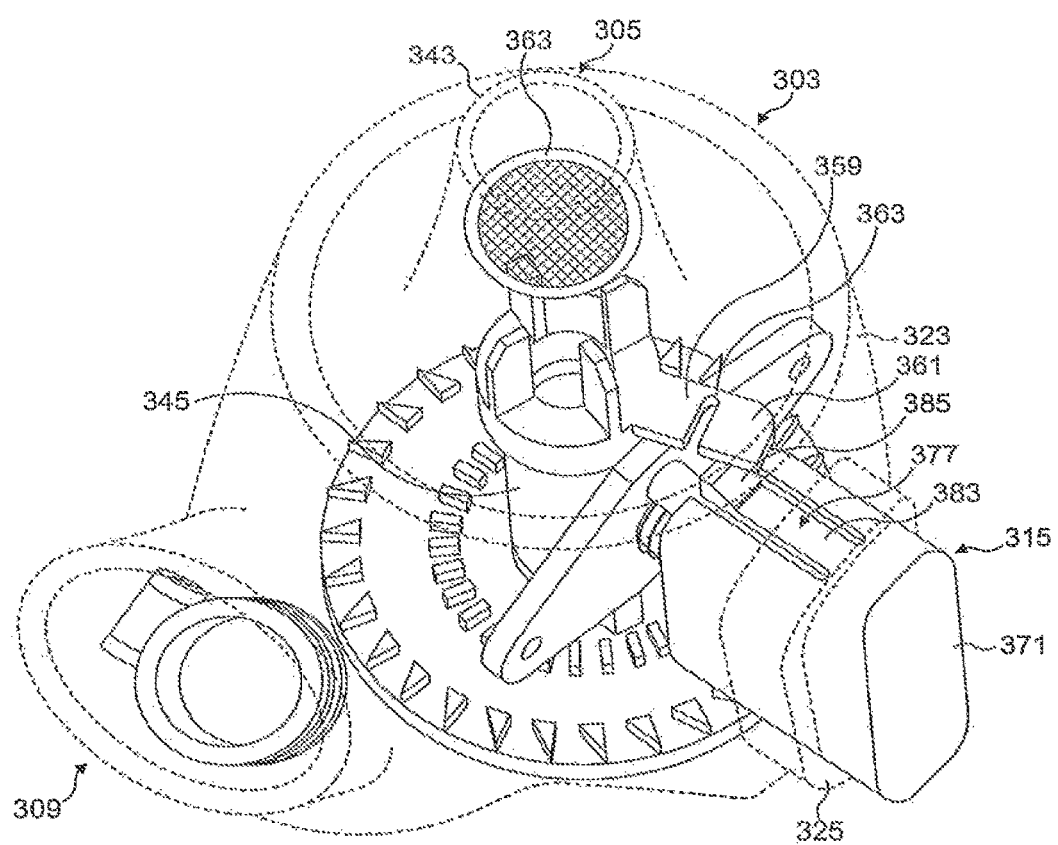
FIG. 20 illustrates a part cut-away fragmentary perspective view of the delivery device of FIG. 18, where the nosepiece unit is being removed from the body assembly and the release member of the nosepiece unit is being deformed by engagement with the latch element of the actuating member of the rupturing mechanism.
Figure 21:
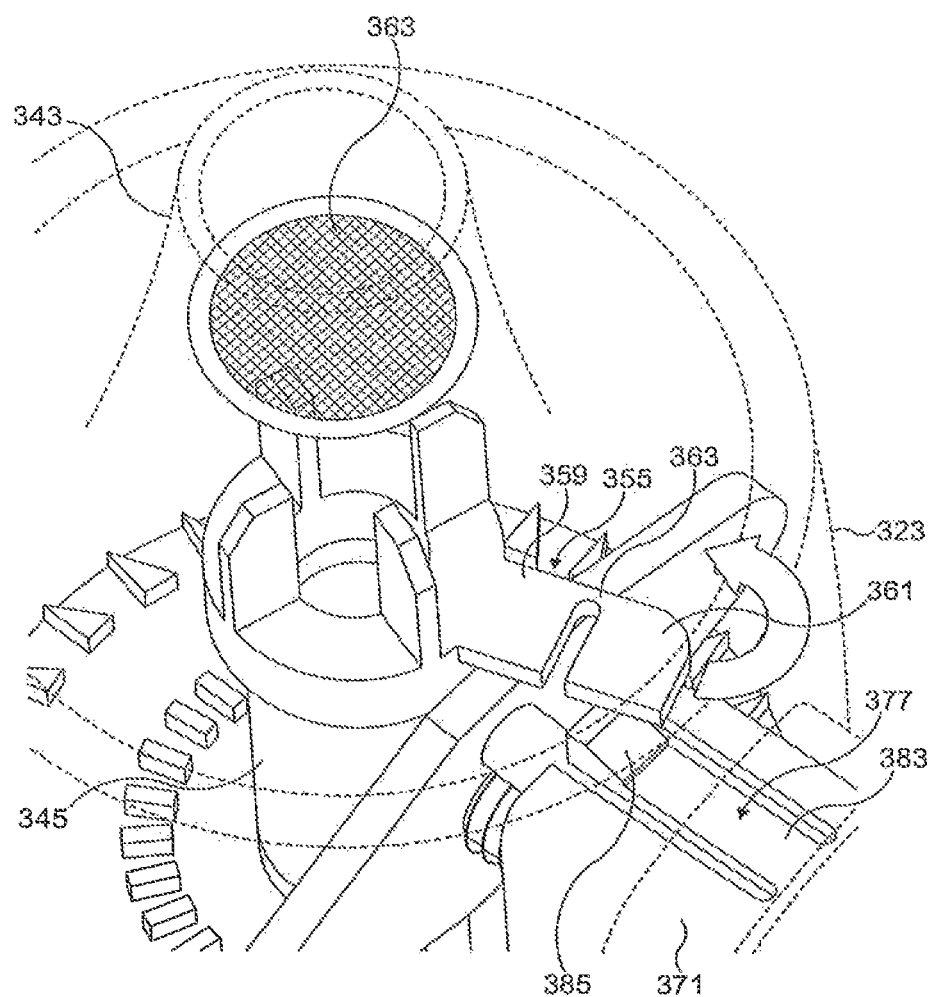
FIG. 21 illustrates the perspective view of FIG. 20 in enlarged scale.
Figure 22:
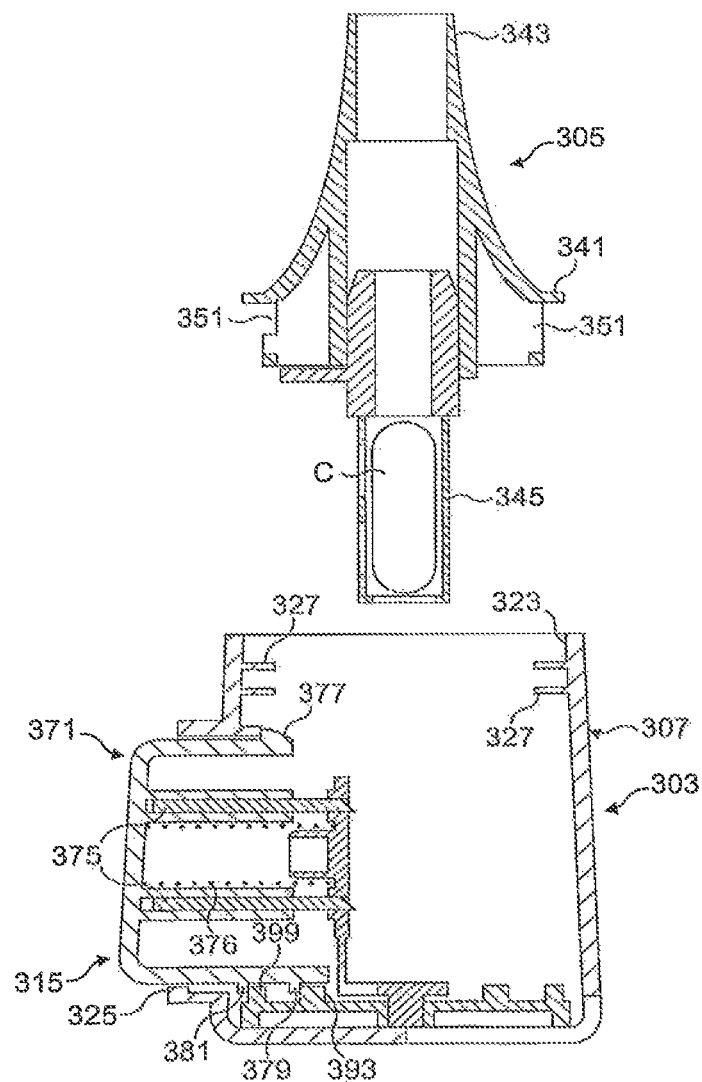
FIGS. 22 to 26 illustrate vertical sectional views of the operative sequence of the delivery device of FIG. 18.
Figure 23:
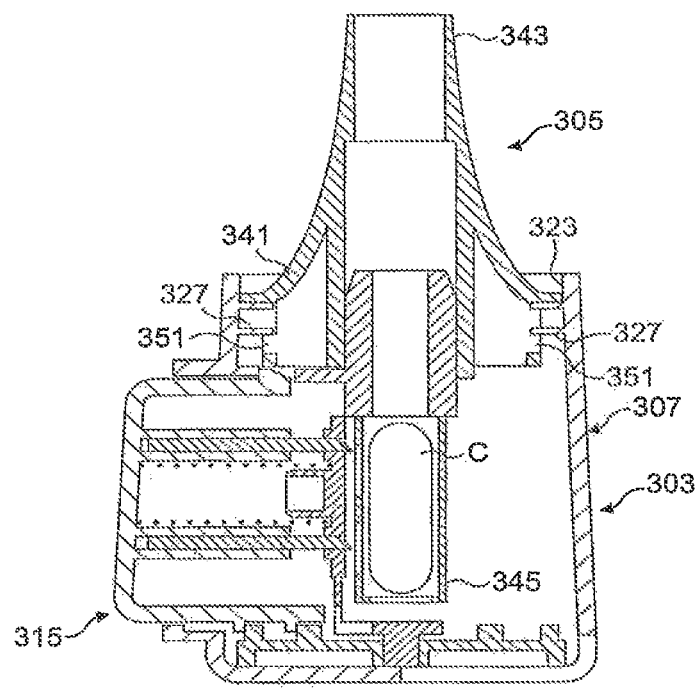
Figure 24:
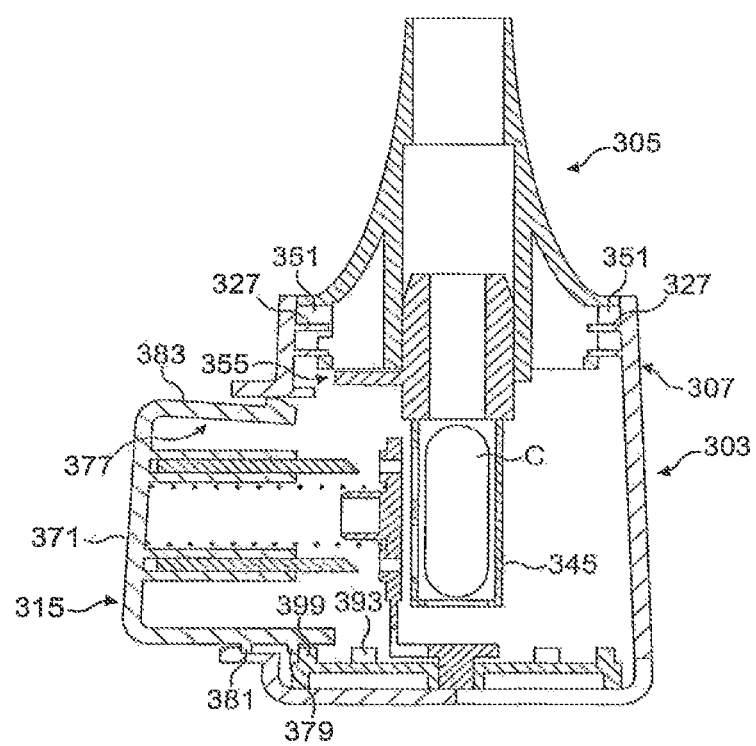
Figure 25:
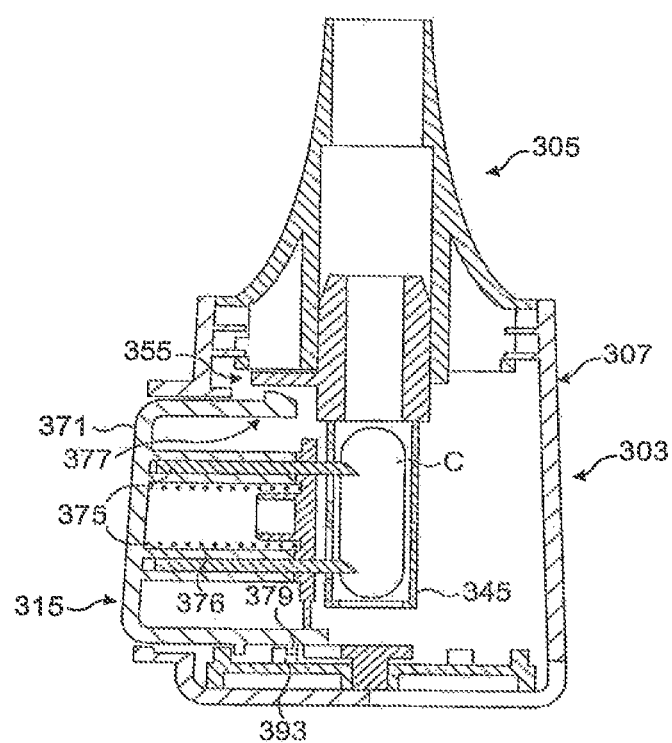
Figure 26:
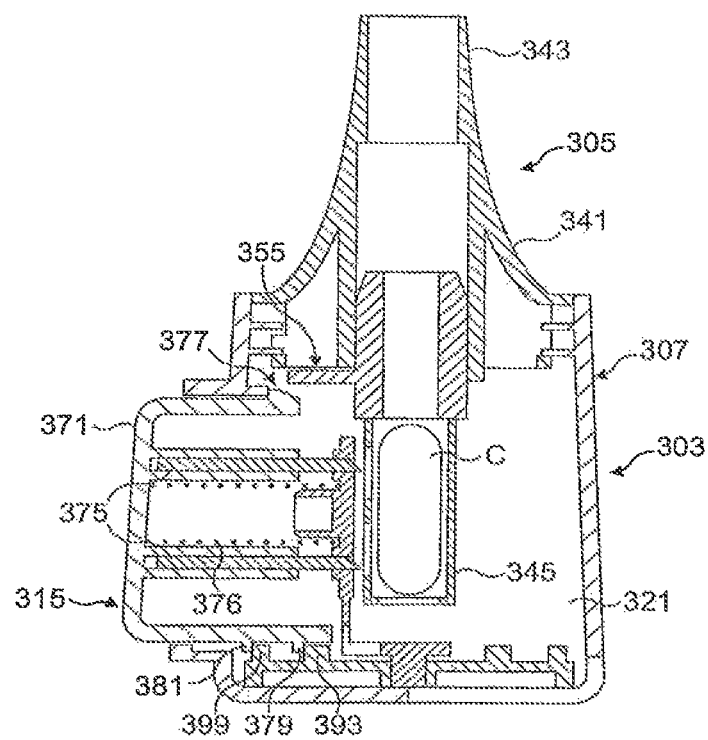

In this embodiment the release member 355 comprises a radially-directed arm, which comprises a support element 359 which is attached to the container chamber 345, an engagement element 361 which is operative to engage the latch member 377 of the actuating member 371 of the rupturing mechanism 315, and a frangible connection element 363, here a flexible, deformable element, which connects the support element 359 to the engagement element 361 in such a manner that the engagement element 361 presents a rigid structure when rotated in the one, fitting sense in fitting the nosepiece unit 305 to the housing 307 and is deformed, here plastically deformed, when rotated in the other, removal sense in removing the nosepiece unit 305 from the housing 307, as represented in FIGS. 20 and 21. In this embodiment the connection element 363 is bent, and permanently deformed, by engagement with the latch member 377 of the actuating member 371 of the rupturing mechanism 315 on removing the nosepiece unit 305 from the housing 307, and this deformation prevents re-use of the nosepiece unit 305, insofar as the release member 355 is no longer operative to release the actuating member 371 of the rupturing mechanism 315 to a release position. With this configuration, the possibility of using a used nosepiece unit 305 is avoided and the subject is thus ensured of receiving a dose of substance with each operation of the device.

In this embodiment the nosepiece unit 305 further comprises a grid 363, here a gauze, which is disposed between the nosepiece 341 and the container chamber 345, such as to prevent the container C or any parts thereof, such as resulting from rupturing of the container C, from passing through the nosepiece 341 and entering the nasal cavity of the subject.

In this embodiment the container chamber 345 and the grid 363, as components which contact the container C and the contained powder, are fabricated from a material having a low moisture sensitivity, here a plastics material, such as to reduce any tendency to become tacky in the presence of moisture, and therefore reduce the tendency for the container C and the powdered substance as contained thereby to adhere to the wall of the container chamber 345 or the grid 363.

In this embodiment the nosepiece 341, as a component which contacts the powdered substance, is fabricated from a material having a low moisture sensitivity, here a plastics material, such as to reduce any tendency to become tacky in the presence of moisture, and therefore reduce the tendency for the powdered substance to adhere to the wall of the nosepiece 341.

In one embodiment the container C is a gelatine capsule.

In another embodiment the container C can be manufactured from a material which has a reduced tendency to become tacky in the presence of moisture, as occurs with gelatine capsules, and therefore reduce the tendency for the container C to adhere to the wall of the container chamber 345 or the grid 363.

In one embodiment the container C is formed of a cellulose derivative, such as hydroxypropyl methylcellulose (HPMC), hydroxypropylcellulose, methylcellulose, ethylcellulose and carboxymethylcellulose In another embodiment the container C can comprise a plastics material, preferably a water insoluble material, such as a polycarbonate.

In one embodiment the container C can be manufactured from a lightweight material, such as thin-wall section polymeric materials, which reduces the energy required to move the container C, typically by one or both of vibration and rotation, and thereby allow the delivery device to be operated at reduced flow rates, which is particularly advantageous for nasal delivery.

In an alternative embodiment the container C can include an outer coating of a material, such as parylene, which has a reduced tendency to become tacky in the presence of moisture, as occurs with gelatine capsules, and therefore reduce the tendency for the container C to adhere to the wall of the container chamber 345 or the grid 363.

In this embodiment, the container C is cylindrical in shape with hemispherical ends.

In other embodiments the container C could have other geometric forms, such as spherical, which allows for efficient powder release at low flow rates.

In this embodiment the rupturing mechanism 315 comprises an actuating member 371, here in the form of a button, which extends through the clearance aperture 325 in the housing 307 and is configured to be depressed by the subject, a piercing element 375, here including two pins, which is supported by the actuating member 371 and operable to drive the piercing element 375 to pierce the container C, and thereby provide for release of the contained powdered substance on the generation of a flow through the container chamber 345 of the nosepiece unit 305, and a biasing element 376, here a compression spring, for normally biasing the actuating member 371 outwardly of the housing 307, such as to withdraw the piercing element 375.

The actuating member 371 includes a latch member 377 which is operative to lock the actuating member 371 in an intermediate position, as illustrated in FIG. 26, in which the piercing elements 375 are withdrawn from the container chamber 345, such as to allow for rotation of the contained container C, and first and second lug members 379, 381 which are operative to operate the locking mechanism 317 and prevent further depression of the actuating member 371 from the intermediate position.

In this embodiment the latch member 377 comprises a resilient arm 383 and a detent 385 at one end of the arm 383, which engages a surface of the housing 307 to latch the actuating member 371 in the intermediate position. In this embodiment the latch member 377 is released, here by deflection of the resilient arm 383, by engagement with the release member 355 of the nosepiece unit 305 in fitting the nosepiece unit 305 to the housing 307. As described hereinabove, the release member 355 of the nosepiece unit 305 is not operative to release the latch member 377 on removal of the nosepiece unit 305 from the housing 307, as the release member 355 is deformed through engagement with the latch member 377.

In this embodiment the locking mechanism 317 comprises a rotatable member 391 which includes a plurality of first engagement elements 393, in this embodiment disposed on a first annulus centred about the rotation axis of the rotatable member 391, and a plurality of second engagement elements 395 which are disposed on a second, larger annulus centred about the rotation axis of the rotatable member 391.

The first engagement elements 393 each include an outwardly-facing, locking surface 397 which, when the actuating member 371 of the rupturing mechanism 315 is in the intermediate position, acts to engage an adjacent first lug 379 of the actuating member 371, such as to prevent depression of the same.

The second engagement elements 395 each include an indexing surface 399 which is engaged by respective ones of the lugs 379, 381 such as to index the rotatable member 351, such that the actuating member 371 of the rupturing mechanism 315 can be depressed to rupture the contained container C following release of the actuating member 371 to the released position and prevent further depression of the actuating member 371 following release of the actuating member 371 to the intermediate position.

In one embodiment the mouthpiece unit 309 could include a heat exchanger which is in fluid communication with the mouthpiece 331 and acts to draw heat from the exhaled air flow as delivered through the mouthpiece 331, thus decreasing the temperature of the air flow as delivered to and downstream of the container member 345. By decreasing the temperature of the air flow, the humidity of the air flow is reduced, with the water vapor condensing in the heat exchanger, and the impact of condensation is significantly reduced, thus allowing for successive doses of powdered substance to be delivered without affecting the release of powdered substance from the containers C.

Operation of the delivery device will now be described hereinbelow.

A subject first takes a nosepiece unit 305 for fitting to the body assembly 303, as illustrated in FIG. 22.

The subject then inserts a nosepiece unit 305 into the fitting aperture 323 in the housing 307, as illustrated in FIG. 23.

The subject then rotates the nosepiece unit 305, in this embodiment in the counter-clockwise sense from above, such as to lock the nosepiece unit 305 to the housing 307, as illustrated in FIG. 24. This rotation of the nosepiece unit 305 causes the release member 355 thereof to engage the latch element 377 of the actuating member 371, such as to release the same, here by deflection of the resilient arm 383 of the latch element 377 through engagement with the release member 355.

The subject then operates the rupturing mechanism 315 to rupture the contained container C, as illustrated in FIG. 25, following which the subject releases the actuating member 371, which returns to the intermediate position, as illustrated in FIG. 26.

The subject then inserts the nosepiece 341 into one of his/her nostrils, grips the mouthpiece 331 in his/her mouth, and exhales through the mouthpiece 331.

The exhaled air flow, where having a sufficient flow rate, is then driven through the cavity 321 in the housing 307 and the container chamber 345, which acts to move the container C, in this embodiment by vibration and rotation, and entrain the powdered substance as contained by the container C.

The exhaled air flow, as then entraining the powdered substance, is delivered though the nosepiece 341 into one nasal cavity of the subject.

In this embodiment the exhaled air flow has such a pressure as to pass around the posterior region of the nasal septum, and into the other nasal cavity, thereby achieving a bi-directional air flow as described in the applicants' earlier WO-A-00/051672.

Following use of the device, the nosepiece unit 305 is then removed from the device assembly 303, in order to allow for the device to be re-used.

The nosepiece unit 305 is removed by rotating the nosepiece unit 305 relative to the housing 307, in this embodiment in a clockwise sense when viewed from above, and withdrawing the nosepiece unit 305 from the fitting aperture 323 in the housing 307.

On rotating the nosepiece unit 305, the release arm 355 of the nosepiece unit 305 engages the latch member 377 of the actuating member 371, in this embodiment through engagement with the engagement element 361 of the release member 355, which causes the connection element 363 of the release member 355 to be bent, and permanently deformed. As described hereinabove, this deformation prevents re-use of the nosepiece unit 305, insofar as the release member 355 is no longer operative to release the actuating member 371 of the rupturing mechanism 315 to the operative position.

Finally, it will be understood that the present invention has been described in its preferred embodiments and can be modified in many different ways without departing from the scope of the invention as defined by the appended claims.

In one embodiment the powdered substance can also be formulated, for example, by coating or blending, such as to reduce the hygroscopicity and transiently increase the dissolution time, and thus reduce any loss of powdered substance in the device due to interaction with condensation on the internal surfaces of the device.

Also, the delivery devices of the described embodiments have been described particularly in relation to the use of capsules. It is to be understood that the present invention has application with any kind of powder delivery system, including blisters, and can be configured as a single-use or multi-use device.

The invention claimed is:

1. A nasal delivery device for delivering a particulate substance to the nasal airway of a subject, the delivery device comprising:

a mouthpiece unit which includes a mouthpiece through which the subject in use exhales;

a nosepiece unit which includes a nosepiece for fitting to a nostril of the subject; and a substance-supply unit which is configured to receive a container containing the particulate substance, the substance-supply unit operable to provide a metered amount of the particulate substance, such that an exhalation air flow delivered through the substance-supply unit entrains the substance;

the substance-supply unit including a support member and a body section that is movable relative to the support member between a first, container-receiving position for receiving a container in which the container is not disposed in fluid communication with the mouthpiece unit and the nosepiece unit, and a second, operative position in which the container is in fluid communication with the mouthpiece unit and the nosepiece unit;

wherein one of the support member and the body section includes an inlet aperture which is fluidly isolated from the mouthpiece unit when the body section is in the container-receiving position and fluidly connected to the mouthpiece unit when the body section is in the operative position.

2. The delivery device of claim 1, wherein the container comprises first and second parts which together define an enclosed chamber and are movable between a first, closed configuration in which the container is closed and a second, open configuration in which the container is open and the substance-supply unit is operable to move the first and second parts of the container to the open configuration.

3. The delivery device of claim 2, wherein the first and second parts of the container are slideably disposed relative to one another and each include at least one aperture, wherein the aperture of the first part and the aperture of the second part are covered when the first and second parts in the closed configuration and the aperture of the first part and the aperture of the second part are uncovered when the first and second parts of the container are in the open configuration.

4. The delivery device of claim 1, wherein the body section is configured to rotate relative to the support member.

5. The delivery device of claim 4, wherein the body section includes a container-receiving aperture, wherein the container-receiving aperture is uncovered when the body section is in the container-receiving position and is covered when the body section is in the operative position.

6. The delivery device of claim 1, further comprising:
a housing which supports the mouthpiece unit, the nosepiece unit and the substance-supply unit.

7. The delivery device of claim 6, wherein the substance-supply unit includes a container-receiving member which is movably disposed between an open position for enabling loading of a container into the container-receiving member, and a closed position in which the container is contained within the housing.

8. The delivery device of claim 7, wherein the container-receiving member includes a cavity which defines an exhalation flow channel between the mouthpiece unit and the nosepiece unit, the exhalation flow channel configured to direct the exhalation air flow through the exhalation flow channel when the subject exhales through the mouthpiece.

9. The delivery device of claim 7, wherein the substance-supply unit includes a locking mechanism for locking the container-receiving member in the closed position.

* * * * *